(12) United States Patent
Ridder et al.

(10) Patent No.: US 8,095,193 B2
(45) Date of Patent: *Jan. 10, 2012

(54) APPARATUS AND METHOD FOR CONTROLLING OPERATION OF VEHICLES OR MACHINERY BY INTOXICATED OR IMPAIRED INDIVIDUALS

(75) Inventors: Trent Ridder, Woodbridge, VA (US); Ben ver Steeg, Redlands, CA (US); James McNally, Albuquerque, NM (US)

(73) Assignee: TruTouch Technologies, Inc., Albuquerque, NM (US)

( * ) Notice: Subject to any disclaimer, the term of this patent is extended or adjusted under 35 U.S.C. 154(b) by 1661 days.

This patent is subject to a terminal disclaimer.

(21) Appl. No.: 11/393,341

(22) Filed: Mar. 30, 2006

(65) Prior Publication Data

US 2006/0173256 A1 Aug. 3, 2006

Related U.S. Application Data

(63) Continuation-in-part of application No. 11/305,964, filed on Dec. 19, 2005, now Pat. No. 7,756,558, which is a continuation-in-part of application No. 10/852,415, filed on May 24, 2004, now Pat. No. 7,403,804, which is a continuation-in-part of application No. 09/832,585, filed on Apr. 11, 2001, now Pat. No. 6,574,490, and a continuation-in-part of application No. 10/281,576, filed on Oct. 28, 2002, now Pat. No. 7,202,091, and a continuation-in-part of application No. 10/378,237, filed on Mar. 3, 2003, now Pat. No. 6,865,408, and a continuation-in-part of application No. 10/753,506, filed on Jan. 8, 2004, now Pat. No. 7,016,713.

(51) Int. Cl.
*A61B 5/1455* (2006.01)
*G08B 13/14* (2006.01)

(52) U.S. Cl. ............ 600/310; 600/322; 340/573.1; 340/576

(58) Field of Classification Search .......... 600/310, 600/322; 340/573.1, 576, 5.82
See application file for complete search history.

(56) References Cited

U.S. PATENT DOCUMENTS

| 6,229,908 B1 * | 5/2001 | Edmonds et al. ............ 340/5.83 |
| 6,560,352 B2 * | 5/2003 | Rowe et al. ............ 340/5.82 |

* cited by examiner

*Primary Examiner* — Eric Winakur
(74) *Attorney, Agent, or Firm* — V. Gerald Grafe

(57) ABSTRACT

The present invention relates generally to non-invasive methods and apparatuses for determining analyte properties of a subject and identity characteristics of a subject. Embodiments of the present invention provide analyte property determination and identity determination or verification from the same spectroscopic information, making unauthorized use or misleading results less likely that in systems that include separate analyte and identity determinations. The invention can be used to prevent operation of automobiles or other equipment unless the operator has an acceptable alcohol concentration, and to limit operation of automobiles or other equipment to authorized individuals who are not intoxicated or drug-impaired.

47 Claims, 22 Drawing Sheets

“APPARATUS AND METHOD FOR CONTROLLING OPERATION OF VEHICLES OR MACHINERY BY INTOXICATED OR IMPAIRED INDIVIDUALS”

CROSS REFERENCES TO RELATED APPLICATIONS

This application claims priority under 35 U.S.C. §120 as a continuation-in-part of U.S. patent application Ser. No. 11/305,964, entitled "Apparatus and Methods for Mitigating the Effects of Foreign Interferents on Analyte Measurements in Spectroscopy," filed Dec. 19, 2005, now U.S. Pat. No. 7,756,558 incorporated herein by reference, which application was a continuation-in-part of U.S. patent application Ser. No. 10/852,415, entitled "Noninvasive determination of alcohol in tissue," filed May 24, 2004, now U.S. Pat. No. 7,403,804 incorporated herein by reference, which application was a continuation in part of U.S. patent application Ser. No. 09/832,585, entitled "System For Non-Invasive Measurement Of Glucose In Humans," filed Apr. 11, 2001, now U.S. Pat. No. 6,574,490 and of U.S. patent application Ser. No. 10/281,576, entitled "Optically Similar Reference Samples", filed Oct. 28, 2002, now U.S. Pat. No. 7,202,091 and of U.S. patent application Ser. No. 10/378,237, entitled "System For Non-Invasive Measurement Of Glucose In Humans," filed Mar. 3, 2003, now U.S. Pat. No. 6,865,408 and of U.S. patent application Ser. No. 10/753,506, "Noninvasive Determination of Direction and Rate of Change of an Analyte," filed Jan. 8, 2004, now U.S. Pat. No. 7,016,713 each of which is incorporated herein by reference.

TECHNICAL FIELD

The present invention relates to an interlock to prevent vehicle or machinery operation by intoxicated or impaired individuals, and more specifically to an interlock that uses spectroscopic information to measure alcohol and/or one or more substances of abuse and to perform a biometric measurement.

BACKGROUND OF THE INVENTION

Alcohol abuse is a national problem that extends into virtually all aspects of society. Over 17,000 people are killed each year in alcohol related traffic accidents due to the detrimental effects of alcohol on motor control and judgment. Given the magnitude of the driving under the influence (DUI) problem, increased attention is being focused on interlocks as a tool to prevent intoxicated individuals from operating motor vehicles and machinery.

The use of alcohol measurement devices to prevent drunk driving has been proposed. Although reflex and response testing methods have been disclosed (see U.S. Pat. No. 5,224,566), the vast majority of disclosed methods involve the use of a breath device to detect either the alcohol in the lungs of the prospective operator or the alcohol present in the air within the passenger compartment (see U.S. Pat. No. 4,592,443, U.S. Pat. No. 5,055,268, U.S. Pat. No. 5,426,415, and US 2004141171A1). In the event of alcohol detection (or detection of alcohol above a threshold), operation of the vehicle is typically prevented via restriction of the ignition system. However, many of the breath-based interlocks are limited in their effectiveness due to numerous methods for circumventing or defeating the test. Principal among these is the absence of inherent proof that the prospective driver is the individual providing the breath sample for the alcohol test, thus potentially allowing individuals other than the driver to provide the breath sample or the driver using an artificial breath sample (e.g. air in a balloon) for the interlock measurement.

In order to address these limitations, several combinations of breath and biometric devices have been disclosed in the art. The most common biometric methods in interlocks are voice recognition (see U.S. Pat. No. 4,738,333 and U.S. Pat. No. 6,748,301), video recognition (see U.S. Pat. No. 6,748,792 and U.S. Pat. No. 6,956,484), and bodily feature identification (see U.S. Pat. No. 4,996,161). In all of these cases, the biometric device relies upon a measurement or action that is distinct from the breath alcohol measurement. Consequently, there is concern over the robustness of the combined measurement methods as well as the potential for the measurement to be defeated by taking advantage of the two distinct measurements. For example, in some situations the potential exists for the biometric measurement to be acquired from one potentially intoxicated individual while the alcohol measurement is acquired from a second, sober individual.

Recently, transdermal alcohol sensors have been disclosed as an alternative to breath and blood alcohol measurements. US 2005230175 A1 discloses the use of a transdermal alcohol sensor as part of an ignition interlock to prevent drunk driving. However, transdermal alcohol measurements require contact between the sensor and skin over long periods of time to measure the alcohol present in perspiration as it leaves the body. The long measurement time represents a significant drawback of transdermal measurements for interlock applications. Furthermore, the transdermal method has no inherent means for subject identification other than the physical attachment of the sensor to a body part. Thus, there is no integral means to ensure that the driver is the person wearing the device, which implies that transdermal interlocks suffer from many of the same limitations currently associated with breath-based interlocks. Improved methods for integrating alcohol and identification measurements are needed.

Spectroscopic measurements, such as those described by Robinson in U.S. Pat. No. 6,278,889 for glucose measurements, offer promise for completely noninvasive alcohol measurements in people. In U.S. Pat. No. 5,743,349, titled "Non-invasive optical blood alcohol concentration reader and vehicle ignition interlock system and method", filed Sep. 23, 1996, since abandoned, Steinberg discloses a vehicle ignition interlock that incorporates a spectroscopic means for noninvasively measuring blood alcohol concentration. Steinberg does not disclose any means for verifying that the spectroscopic measurement is acquired from the prospective driver.

Furthermore, Steinberg discloses the measurement of electromagnetic radiation in the 250 to 3000 nm wavelength range by introducing radiation to a finger and measuring the light exiting the opposite side of the finger. Such transmission approaches, while potentially feasible in the visible region (400 to 800 nm), are limited by the strong absorption of water (water is a major component of the tissue) in the near and mid-infrared regions (>800). For tissue samples greater than a few millimeters in thickness, the absorption of water results in virtually no measurable radiation exiting the opposite side of the sample. Consequently, little if any radiation remains for subsequent measurement of alcohol concentration.

In U.S. Pat. No. 6,229,908, titled "Driver Alcohol Ignition Interlock", filed Apr. 22, 1997, Edmonds and Hopta disclose an ignition interlock incorporating a spectroscopic alcohol measurement of the finger combined with a means for generating a finger print image. The finger print image is intended to identify the operator in order to ensure that the alcohol measurement was acquired from the prospective driver and not a passenger. Similar to existing breath-based interlocks, the finger print image is obtained from a measurement that is distinct from the spectroscopic measurement, thereby yielding potential for circumventing the interlock.

SUMMARY OF THE INVENTION

An effective vehicle or machinery interlock can be considered in terms of three primary components. FIG. 1 is a schematic illustration of an embodiment of such an interlock system. A first component is a system 1 that can measure the alcohol concentration of a prospective operator. A second component 2 is a system that can verify that the alcohol measurement was obtained from a specific prospective operator rather than another individual. A third component 3 is a system that can prevent or control operation of the vehicle or machinery. The present invention links the first two components of the disclosed interlock methods via a single spectroscopic measurement, which eliminates the circumvention problems that limit current approaches. For demonstrative purposes the discussion herein generally refers to infrared and near-infrared spectroscopic measurements; visible (UV-vis), Raman, and fluorescence spectroscopic measurements are also feasible techniques for the present invention, Absorption spectroscopy is a generally known analytical method. In some forms, absorption spectroscopy measures the electromagnetic radiation (typical wavelength range of 0.3-25 µm) that a substance absorbs at various wavelengths, though other methods measure other effects a substance has on incident light. Absorption phenomena can be related to molecular vibrations and shifts in energy levels of individual atoms or electrons within a molecule. These phenomena cause the absorbing molecule or atom to switch to a higher energy state. Absorption occurs most frequently in limited ranges of wavelengths that are based upon the molecular structure of the species present in the measured sample. Thus, for light passing through a substance at several wavelengths, the substance will absorb a greater percentage of photons at certain wavelengths than it will at others.

At the molecular level, many primary vibrational transitions occur in the mid-infrared wavelength region (i.e., wavelengths between 2.5-6 µm). However, for some measurements, use of the mid-infrared region can be problematic because molecules with strong absorbance properties (e.g. water) can result in the total absorption of virtually all light introduced to the sample being measured. Typically, the problem is overcome through the use of shorter wavelengths (typically in the near infrared region of 0.7-2.5 µm) where weaker overtones and combinations of the mid-infrared vibrations exist. Thus, the near-infrared region can be employed in such situations as it preserves the qualitative and quantitative properties of mid-infrared measurements while helping to alleviate the problem of total light absorption.

As mentioned above, alcohol and other analytes absorb light at multiple wavelengths in both the mid- and near-infrared range. Due to the overlapping nature of these absorption bands, reliable analyte measurements can be very difficult if only a single wavelength were used for analysis. Thus, analysis of spectral data can incorporate absorption characteristics at several wavelengths, which enables sensitive and selective measurements of the desired attributes. In multi-wavelength spectroscopy, multivariate analysis techniques can be used to empirically determine the relationship between measured spectra and a property of interest (e.g. analyte concentration).

Advances in optical materials and multivariate algorithms over the last several decades have created the potential for expanding spectroscopic measurements into new areas of interest. One such area is noninvasive measurements of analytes in skin. Human skin (FIG. 2) is a multilayer system comprised of the epidermis, dermis, and subcutaneous layers. Each layer has different physiological and chemical characteristics that influence its relative contribution to spectroscopic measurements of tissue. For example, the subcutaneous layer is largely comprised of lipids that are typically absent in other tissue layers. In contrast, the dermal layer is composed primarily of water and collagen. As a result, the spectroscopic measurement of the present invention inherently contains contributions of the analytes within each tissue layer and therefore provides insight into both the chemical composition and the structure of the tissue.

In many cases the complexity of the spectroscopic tissue measurements necessitates application of multivariate models in order to elucidate the property of interest (e.g. alcohol concentration or biometric identification/verification). In some applications, such as the interlock methods of the present invention, the inherent spectral complexity can be advantageous. Due to natural physiological variation in skin, people have different tissue properties (e.g. dermal hydration, collagen densities, and tissue layer thicknesses). The spectroscopic measurement captures the inter-subject differences which enables discrimination between individuals. In other words, the noninvasive spectroscopic signal of the present invention simultaneously enables both analyte (alcohol or substances of abuse) and biometric measurements thereby providing and integrally linking two of the three components of an effective interlock method.

The final component of an effective interlock is a means for preventing operation of the machinery or vehicle. The majority of existing interlock methods disclosed in the art generally involve disruption of the ignition system of the vehicle. A variety of such ignition disruption devices have been disclosed in the art, all of which are suitable for the embodiments described in the present invention. However, other means for preventing operation are also effective. For example, an interlock method incorporating a transmission, brake, computer, engine control system, or steering wheel interlock can be equally suitable for preventing operation of the vehicle or machinery. In some cases, such alternatives to ignition interlocks are advantageous as it enables the operation of vehicle accessories (e.g., radio, safety equipment, etc.) without allowing full operation of the vehicle. Furthermore, the non-invasive nature of the interlock methods of the present invention enable embodiments that are transparent and non-intrusive to lawful, unimpaired drivers.

The advantages and features of novelty that characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

DETAILED DESCRIPTION OF THE INVENTION

Figure 1:
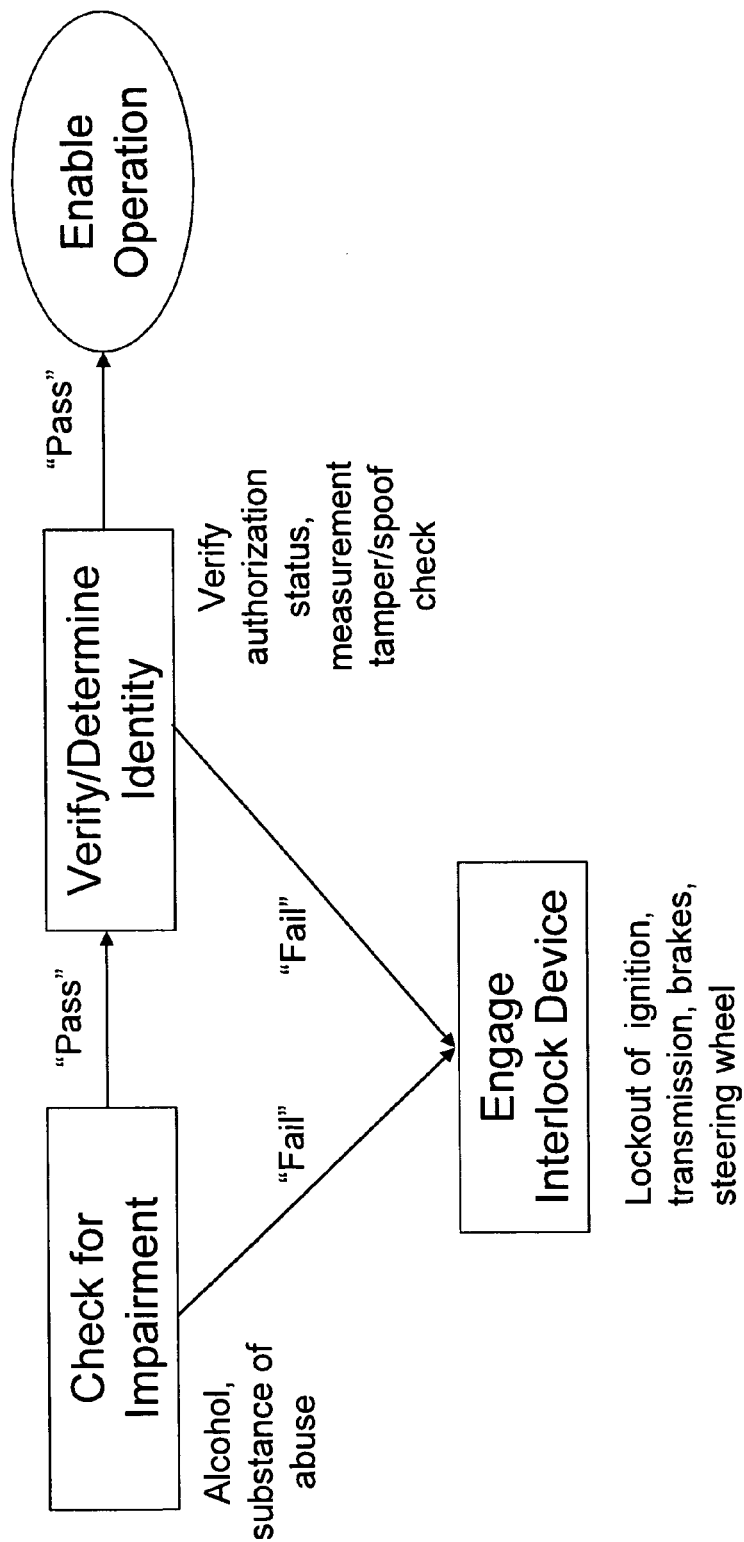
FIG. 1 is a schematic illustration of an interlock system.

In U.S. patent application Ser. No. 10/852,415, entitled "Noninvasive determination of alcohol in tissue," filed May 24, 2004 and incorporated herein by reference, Ridder et al. disclose a method for the noninvasive measurement of alcohol based on spectroscopic techniques that provides an alternative to the current blood, breath, urine, saliva, and transdermal methods. The device requires passive contact between the noninvasive device and a tissue surface such as a finger, forearm, palm, or earlobe in order to measure the alcohol concentration in the tissue. The alcohol measurement described in Ridder typically requires only a short period of time (i.e. 1 minute or less) and thus is suitable for use in vehicle interlocks.

In U.S. Pat. No. 6,628,809, titled "Apparatus and method for identification of individuals by near-infrared spectrum", and in U.S. Pat. No. 6,560,352, titled "Apparatus and method of biometric identification or verification of individuals using optical spectroscopy", both incorporated herein by reference, Rowe et. al. disclose spectroscopic methods for determining the identity or verifying the identity of an individual using spectroscopic measurements of tissue. Such spectroscopic methods provide an alternative to the existing fingerprint, voice recognition, video recognition, and bodily feature identification for vehicle and machinery interlocks.

An advantage of the present invention is that the spectroscopic signal used to measure alcohol concentration, such as that described in Ser. No. 10/852,415, also contains chemical and structural biometric information of the individual being measured as discussed in U.S. Pat. No. 6,628,809 and U.S. Pat. No. 6,560,352. As the spectroscopic signal inherently contains both alcohol and biometric information, the two measurements are integrally linked, which results in a more robust interlock that is not susceptible to many of the limitations of existing interlock methods. The spectroscopic measurement of analytes can also be combined with other identification approaches (e.g., to produce a system that identifies an individual and indicates the presence or concentration of alcohol or a substance of abuse), and with other interlock systems alone (e.g., to prevent operation of an automobile by any intoxicated or drug-using person) or with identification (e.g., to limit operation of equipment to authorized individuals who are not intoxicated).

Another aspect of the present invention is the ability to incorporate the measurement of analytes other than alcohol into the interlock system. For example, spectroscopic methods, such as those described by Miller et. al. in "Minimally invasive spectroscopic system for intraocular drug detection", Journal of Biomedical Optics 7(1), 27-33, have been applied to the detection and quantification of substances of abuse. As such the noninvasive spectroscopic measurement described in Ridder will contain the spectroscopic signals of substances of abuse if present within the measured tissue. From the perspective of the present invention, interlock methods based upon the combination of noninvasive spectroscopic measurements of alcohol or substances of abuse with an explicitly linked spectroscopic biometric measurement represents a significant advantage relative to existing interlock methods.

Detailed embodiments of the present invention are disclosed herein. However, it is to be understood that the disclosed embodiments are merely exemplary of the present invention that can be embodied in various systems. Therefore, specific details disclosed herein are not to be interpreted as limiting, but rather as a basis for the claims and as a representative basis for teaching one of skill in the art to variously practice the invention.

For the purposes of this invention, the term "analyte concentration" generally refers to the concentration of an analyte such as alcohol. The term "analyte property" includes analyte concentration and other properties, such as the presence or absence of the analyte or the direction or rate of change of the analyte concentration, that can be measured in conjunction with or instead of the analyte concentration. While the term "analyte" generally refers to alcohol, other chemicals, particularly substances of abuse and alcohol byproducts, can also benefit from the present invention. For the purposes of this invention, the term "alcohol byproducts" includes the adducts and byproducts of the metabolism of alcohol by the body including, but not limited to, acetone, acetaldehyde, and acetic acid. The term "substances of abuse" refers to, but is not limited to, THC (Tetrahydrocannabinol or marijuana), cocaine, M-AMP (methamphetamine), OPI (morphine and heroin), OxyContin, Oxycodone, and PCP (phencyclidine). The present invention addresses this need for analyte measurements of samples utilizing spectroscopy where the term "sample" generally refers to biological tissue. The term "subject" generally refers to a person from whom a sample measurement was acquired. The term "equipment" means anything whose operation is desired to be controlled based on the identity, current state (e.g., alcohol concentration), or both, of a prospective operator, including, as examples, vehicles, automobiles, trucks, tractors, airplanes, trains, construction equipment, and machinery.

For the purposes of this invention the term "dispersive spectrometer" indicates a spectrometer based upon any device, component, or group of components that spatially separate one or more wavelengths of light from other wavelengths. Examples include, but are not limited to spectrometers that use one or more diffraction gratings, prisms, holographic gratings. For the purposes of this invention the term "interferometric/modulating spectrometer" indicates a class of spectrometers based upon any device, component, or group of components that either modulate different wavelengths of light to different frequencies in time or selectively transmits or reflects certain wavelengths of light based upon the properties of light interference. Examples include, but are not limited to Fourier transform interferometers, Hadamard spectrometers, Sagnac interferometers, mock interferometers, Michelson interferometers, one or more etelons, acousto-optical tunable filters (AOTF's), and one or more LED's or VCSEL's that are scanned or modulated. One skilled in the art recognizes that spectrometers based on combinations of dispersive and interferometric/modulating properties, such as those based on lamellar gratings, are also suitable for the present invention.

The invention makes use of signals, described in some of the examples as absorbance or other spectroscopic measurements. Signals can comprise any measurement obtained concerning the spectroscopic measurement of a sample or change in a sample, e.g., absorbance, reflectance, intensity of light returned, fluorescence, transmission, Raman spectra, or various combinations of measurements, at one or more wavelengths. Some embodiments make use of one or more models, where such a model can be anything that relates a signal to the desired property. Some examples of models include those derived from multivariate analysis methods such as partial least squares regression (PLS), linear regression, multiple linear regression (MLR), classical least squares regression (CLS), neural networks, discriminant analysis, principal components analysis (PCA), principal components regression (PCR), cluster analysis, and K-nearest neighbors. Single or multi-wavelength models based on the Beer-Lambert law are special cases of classical least squares and are thus included in the term multivariate analysis for the purposes of the present invention.

The following detailed description should be read with reference to the drawings. The drawings, which are not necessarily to scale, depict illustrative embodiments that are not intended to limit the scope of the invention. For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure.

As mentioned above, effective interlock methods for preventing an intoxicated or impaired person from operating machinery or a vehicle are comprised of three essential components. The first component is a means for measuring the alcohol (or substance of abuse) concentration in the person and determining if said concentration is above or below a given threshold (e.g. zero if no alcohol is permitted). The second component is a means for determining that the desired person (or member of an authorized group of people) is being measured, rather than another individual, and that the person is appropriately complying with the measurement procedure (e.g. no attempts to spoof or fool the measurement). The final component of an effective interlock is a means for inhibiting or preventing the operation of the machinery or vehicle if it is determined that the person is intoxicated or impaired.

Background of Tissue and Origins of the Spectroscopic Signal

Figure 2:
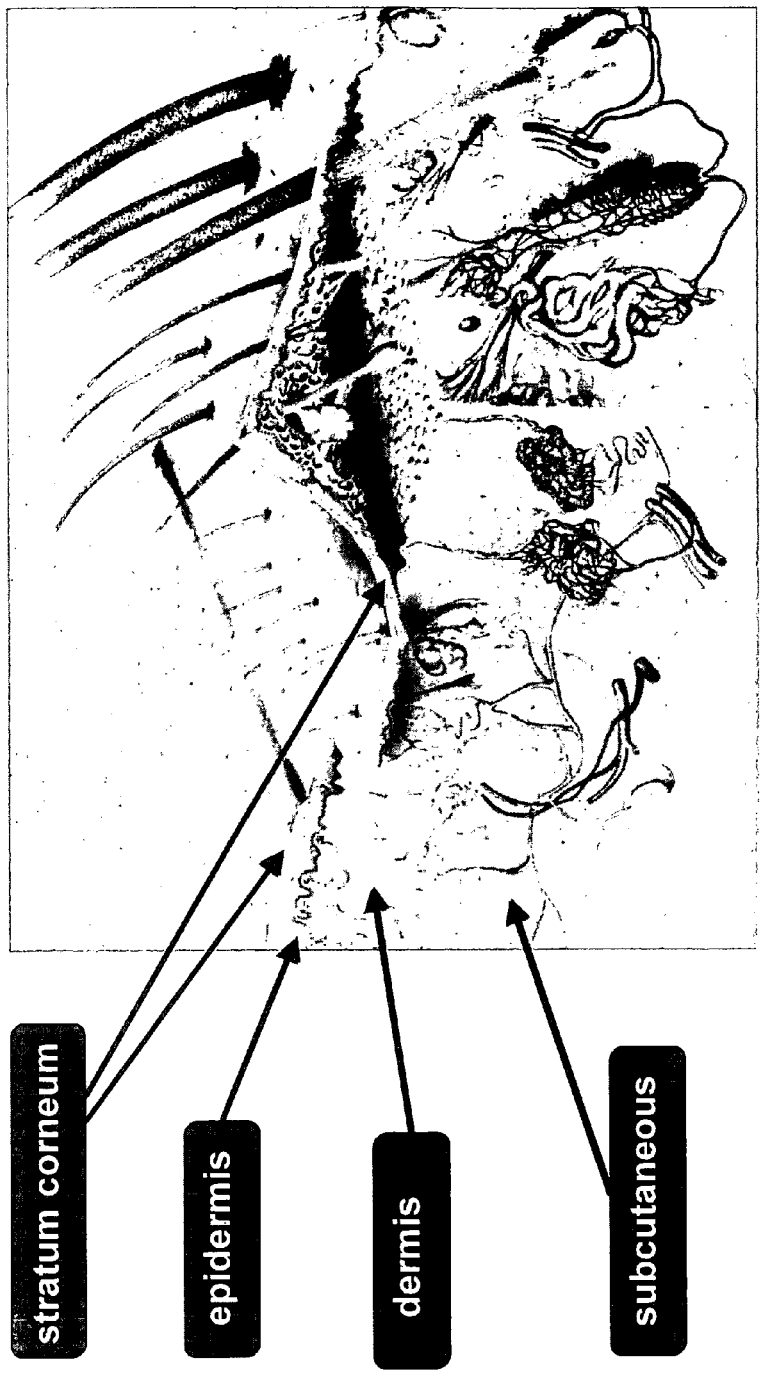
FIG. 2 is a diagram of the layered structure of human skin.

Human skin (FIG. 2) is comprised of epidermal, dermal, and subcutaneous layers, each of which has different physiological and chemical characteristics that influence their relative utility for alcohol measurements. The epidermis contains very little extracellular fluid, and therefore contains minimal information about hydrophilic analytes such as alcohol. The subcutaneous layer is largely comprised of lipids that have low water (and alcohol) solubility which make it poorly suited to alcohol measurements. However, the dermal layer has high water content (generally around 65%) and an extensive capillary bed conducive to the transport of alcohol, which makes it a useful layer of skin tissue for alcohol (or any analyte with high water solubility) measurements.

The layered structure of the tissue provides a wealth of spectroscopic information that can be used to discriminate between people. This biometric signal is a function of many skin properties such as the relative thicknesses of the tissue layers, their scattering coefficients, and the analyte concentrations within each layer. For example, the subcutaneous layer is largely comprised of lipids that are typically absent in other tissue layers. In contrast, the dermal layer is composed primarily of water and collagen. As a result, the spectroscopic measurement contains the relative signal contributions of these analytes and therefore provides insight into both the chemical composition and structure of the tissue. Because different people have different tissue properties (dermal hydration, collagen densities, tissue layer thicknesses), the spectroscopic measurement simultaneously captures both analyte signals (e.g. alcohol signal) and the inter-subject differences that collectively form the biometric signal.

Figure 3:
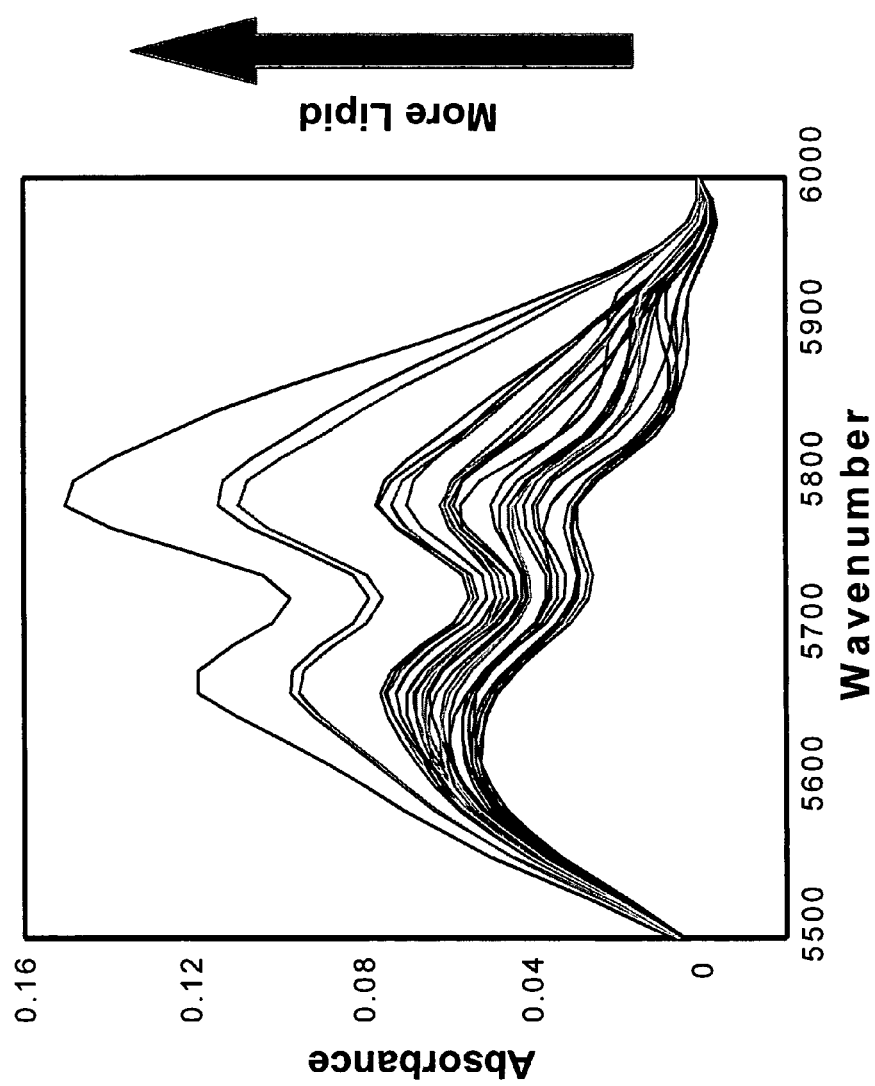
FIG. 3 shows the lipid signals obtained from spectroscopic measurements of 31 individuals.
Figure 4:
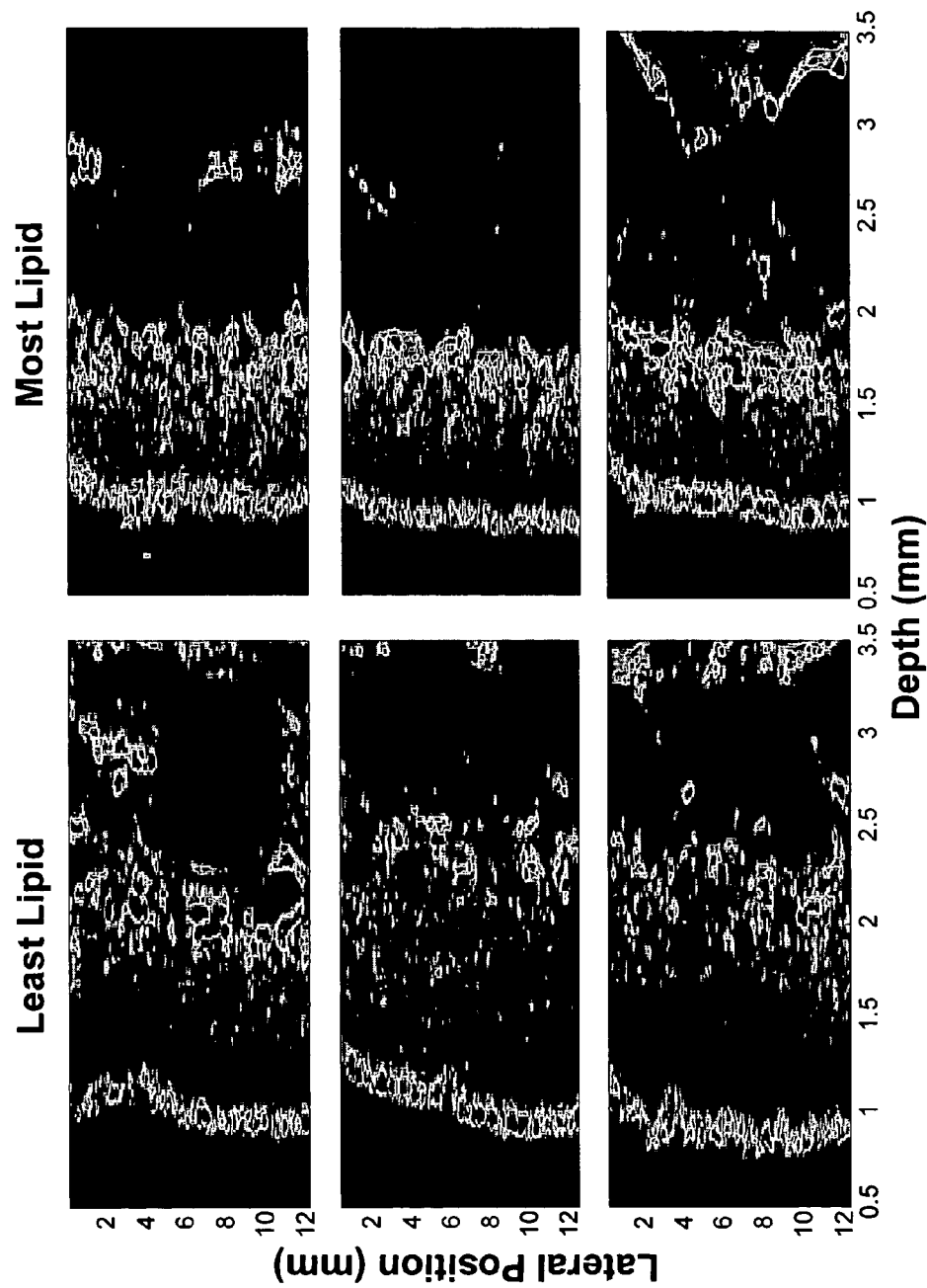
FIG. 4 shows ultrasound images of 6 individuals that demonstrate the difference in tissue structure between people.

FIGS. 3 and 4 combine to provide an example of the inter-subject discriminatory power of the spectroscopic signal. FIG. 3 shows the 5500-6000 $cm^{-1}$ region of NIR spectra obtained from 31 subjects. The pronounced peaks at 5675 and 5800 $cm^{-1}$ correspond to the spectral signature of lipids, which is an indicator that a portion of the NIR signal originated in the subcutaneous tissue layer for some of the 31 subjects. The variation of the lipid signature suggests that the subjects with weaker lipid signal have thicker epidermal and dermal tissue layers, thus preventing the NIR light from reaching the deeper subcutaneous layer where lipids are located. FIG. 4 offers a different perspective that shows ultrasound images that were obtained from 3 of the 31 subjects who exhibited a strong lipid signal and 3 subjects of the 31 that exhibited no discernable lipid signal. In ultrasound images of tissue, a large signal (brighter parts of the image) generally corresponds to a boundary between layers. As such, the strong signal near 1 mm of depth in each window of FIG. 3 corresponds to the ultrasound probe-epidermal interface. The next region of interest is the dermal-subcutaneous boundary, which generally occurs between 1.5 mm and 2.5 mm of depth. Comparison of the two groups demonstrates a marked difference in dermal thickness between the strong and weak lipid signal subjects. Consequently, the magnitude of the lipid signal is of interest because it provides chemical and structural information that can be used to differentiate subjects.

Figure 5:
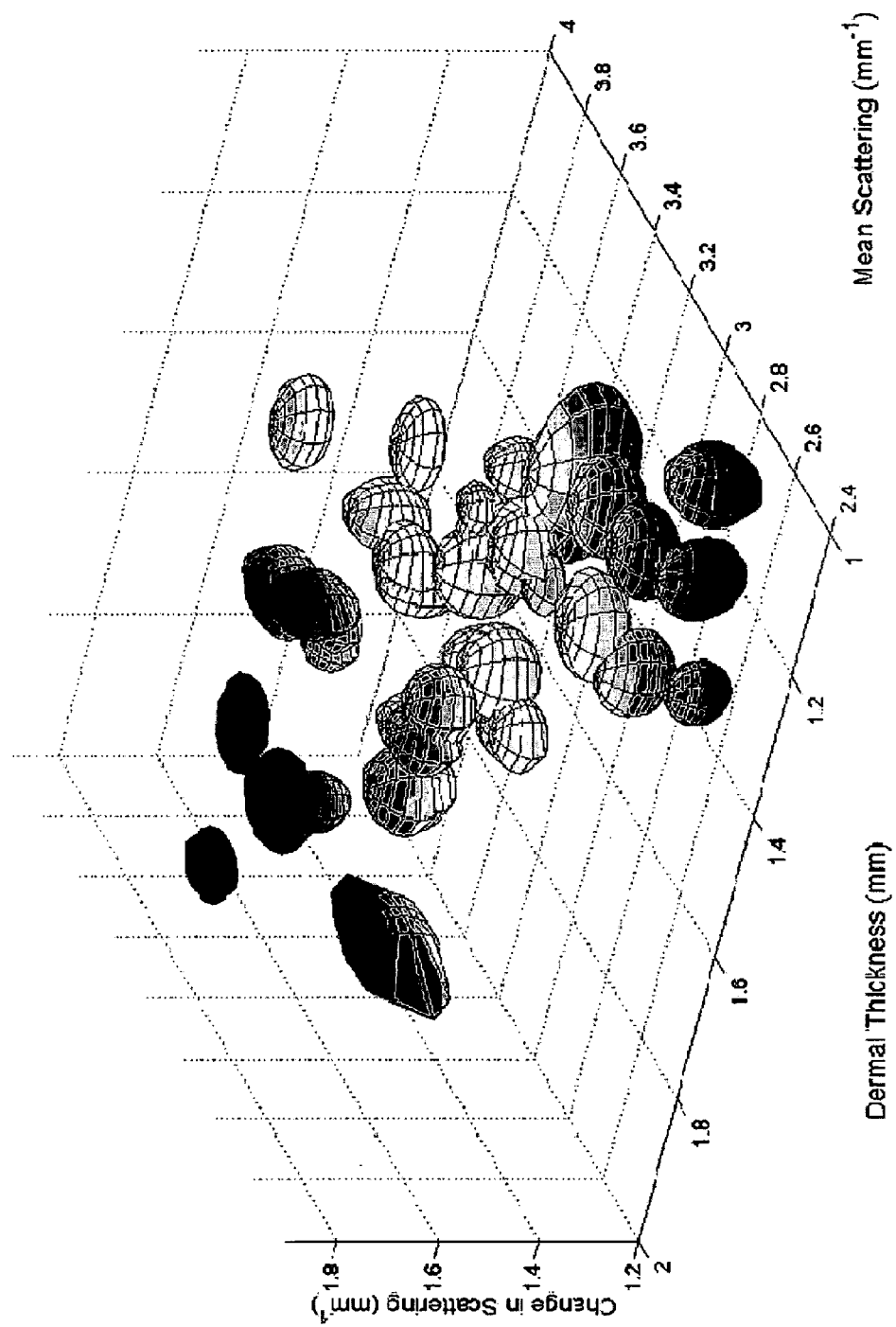
FIG. 5 is a diagram showing the inter-subject discriminatory power of the spectroscopic measurement of the present invention.

While lipid content provides an intuitive example of a discernable property in the spectroscopic measurement, multiple structural and chemical properties can be extracted. In aggregate, these properties form a powerful technique to discriminate between people. FIG. 5 is a visual presentation of the inter-subject resolving power of the measurement using 3 extracted properties. Each ellipsoid in FIG. 5 encompasses the properties extracted from multiple measurements (typically 10-15) obtained from a single subject. Even with only three properties, the measurements acquired from each subject reside in a distinct region of the 3-dimensional space. This example can be extended to include additional properties and thereby further improve the discriminatory power of the biometric signal. The extracted properties can be representative of physical variables (e.g. dermal thickness or scattering coefficient) or purely mathematical (e.g. factors from a principal components analysis, PCA).

The present invention obtains the first two components of the disclosed interlock methods from a single spectroscopic measurement of tissue (e.g., skin). Some demonstrative embodiments of suitable spectroscopic measurement devices are described below. These examples should not be construed as limiting to the invention as one skilled in the art recognizes that other embodiments exist that serve substantially the same function. For example, while the majority of the disclosure relates to near infrared spectroscopic measurements, Raman measurements (and therefore Raman spectrometers) are also suitable for the present invention.

Embodiments for Measuring the Spectroscopic Signal

Figure 6:
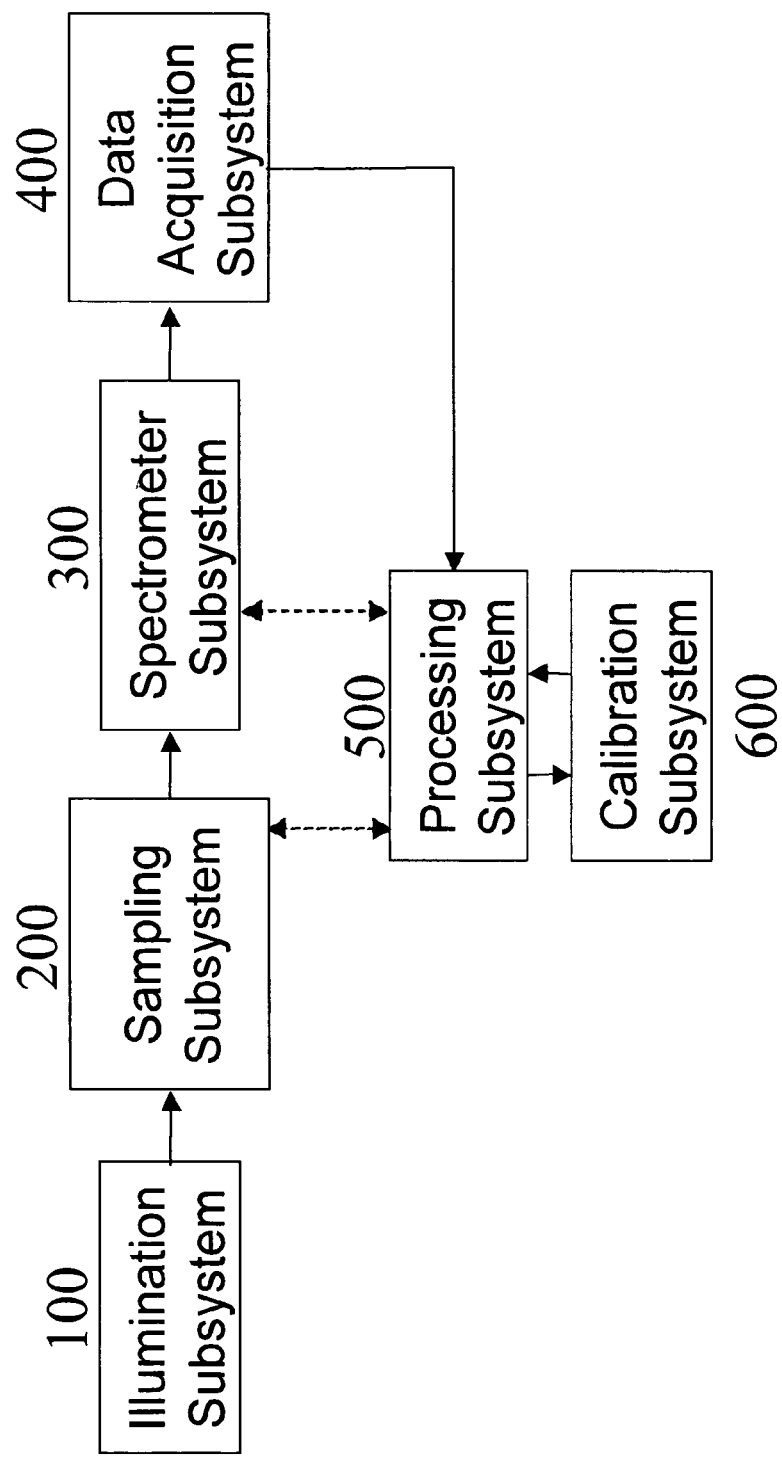
FIG. 6 is a schematic depiction of a system according to the present invention.
Figure 7:
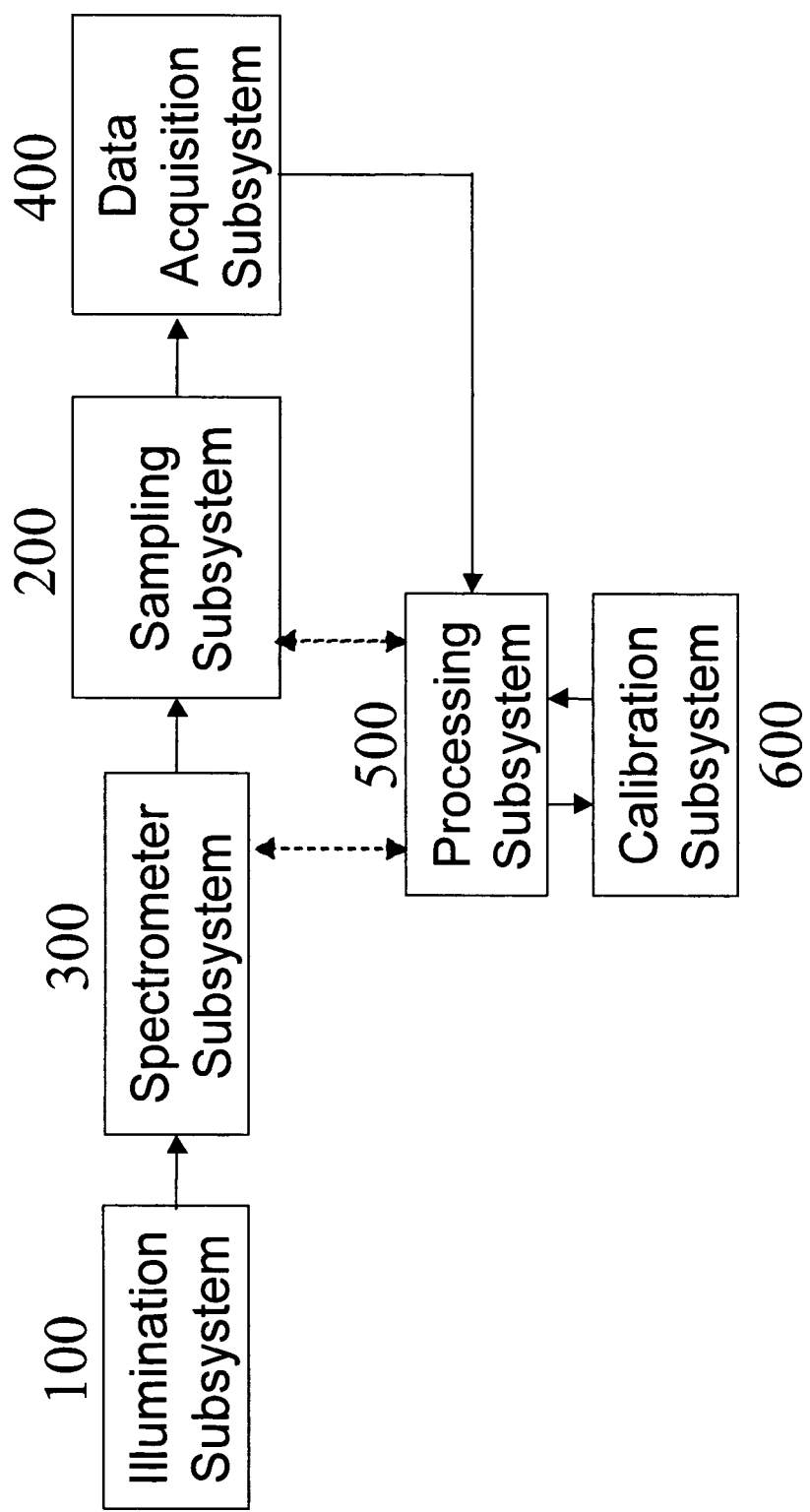
FIG. 7 is a schematic depiction of a system according to the present invention.

Several embodiments of the present invention include an apparatus for measuring the spectroscopic signal of tissue, typically skin. As an example of such an apparatus, FIG. 6 shows a schematic depiction of a non-invasive measurement device. The overall system can be viewed for discussion purposes as comprising six subsystems; those skilled in the art will appreciate other subdivisions of the functionality disclosed. The subsystems include an illumination subsystem 100, a sampling subsystem 200, a spectrometer subsystem 300, a data acquisition subsystem 400, a processing subsystem 500, and a calibration subsystem 600. The subsystems can be designed and integrated in order to achieve a desirable signal-to-noise ratio and performance. FIG. 7 is a schematic depiction of an alternative arrangement of the elements shown in FIG. 6: the spectrometer subsystem and sampling subsystem have been exchanged relative to the system of FIG. 6. Those skilled in the art will appreciate the effect of interchanging elements and subsystems in an optical path. The subsequent discussion assumes the arrangement of FIG. 6 for simplicity, but is not meant to preclude alternative arrangements of the subsystems.

In some embodiments of the present invention, the illumination subsystem 100 generates the near-infrared (NIR) light to interrogate the skin tissue. In an exemplary embodiment, the illumination subsystem contains a broadband, polychromatic light source that emits radiation in the NIR portion of the spectrum. The light source can also emit radiation outside of the NIR. An example of a suitable light source is a tungsten filament lamp. Another example light source is a resistive element such as those commonly used as igniters for furnaces and stoves. These light sources have a lower color temperature than standard filament lamps and are therefore more efficient in the near-infrared spectral region. These sources also have comparatively large emissive surfaces that are less sensitive to spatial effects that are encountered throughout the lifetime of the light source. An additional advantage of igniter-based light sources is a substantially longer lifetime when compared to filament lamps.

Polychromatic sources can also be generated by combining multiple monochromatic or narrow band sources. For example, multiple light-emitting diodes (LED's) and/or vertical cavity surface emitting lasers (VCSEL's) can be combined to form a broad-band polychromatic light source. Various optical methods can be used to combine the outputs of the various individual light sources into a single beam. Such methods include, but are not limited to, reflective integrating chambers, diffuse integrating chambers, a light homogenizer or light pipe, and optical fibers. The output intensities of the discrete light sources can also be independently modulated at predetermined frequencies.

In some embodiments, such as those employing Raman spectroscopy, a monochromatic source is used. Solid state or gas lasers are suitable light sources in these embodiments. Some examples lasers include but are not limited to diode, vertical cavity surface emitting lasers (VCSEL's), NdYg, and HeNe lasers. Polychromatic light sources are also feasible if they are sufficiently narrowed using optical filters. Other illumination systems that can be suitable with embodiments of the present invention are described by Johnson in U.S. Pat. No. 6,862,091, issued Mar. 1, 2005, by Ridder in U.S. Pat. No. 6,684,099, issued Jan. 27, 2004, and by Maynard in U.S. Pat. No. 6,654,125, issued Nov. 25, 2003, each of which is incorporated herein by reference.

Figure 8:
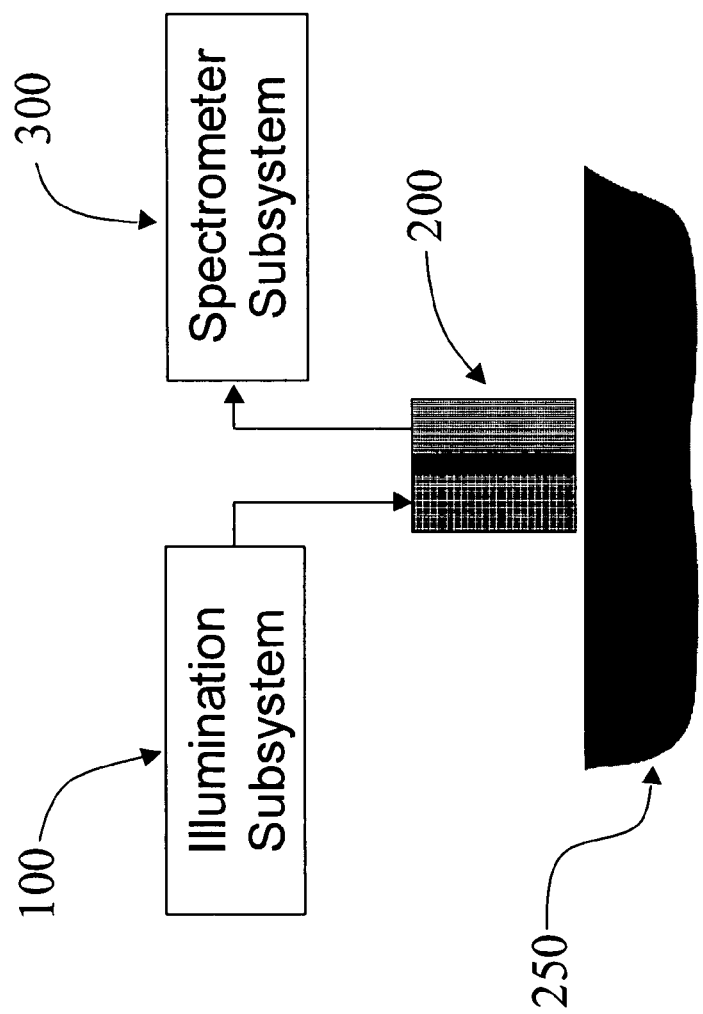
FIG. 8 is a schematic depiction of a system that measures a sample in reflectance.
Figure 9:
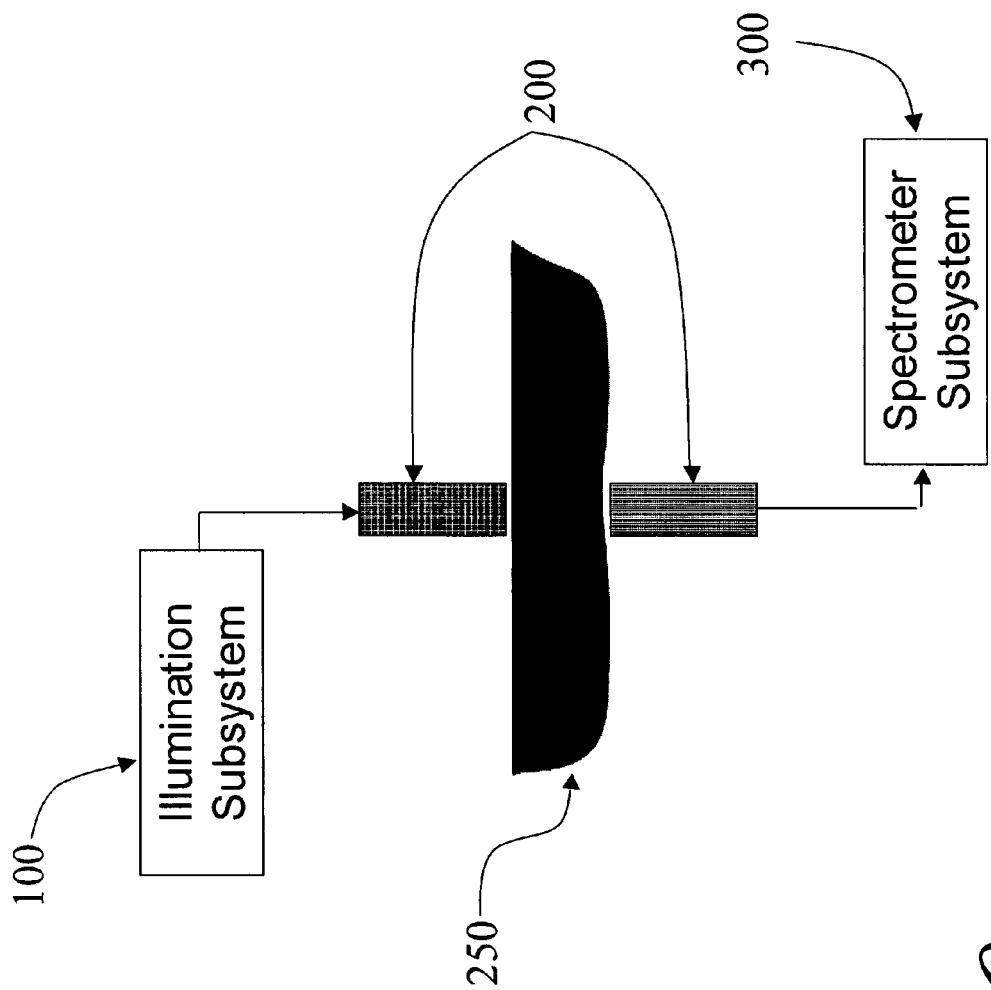
FIG. 9 is a schematic depiction of a system that measures a sample in transmission.

In practicing the method of the present invention, an area of the sample is selected as the point of analysis for the sampling subsystem 200. In the case of noninvasive tissue measurements, this area can include the finger, palms, wrists, earlobe, forearms and any other skin surface. Further, even in the case of using fingers, the present invention allows use of multiple sites along the area. For example, the finger can be measured on both the dorsal and ventral surfaces. Embodiments of the sampling subsystem 200 can be such that light is introduced and collected from the sample 250 in either reflectance or transmission geometries (shown in FIGS. 8 and 9, respectively). A preferred embodiment of the sampling subsystem 200 measures the underside of the forearm using reflectance geometry, and will be used to describe various embodiments of the present invention.

Another advantage of the present invention is that it, unlike fingerprint readers, can use different fingers (or other sites) for enrollment and for subsequent verification. This capability provides for increased enrollment efficiency since the user only has to present one enrollment site to the system, but also provides critical flexibility during the use of the device. An example of this flexibility is the case where the user has enrolled a site on a particular hand and that particular site is unavailable for subsequent analysis due to some injury or some severe surface contamination of the site. This spectroscopic-based biometric system of the present invention can operate on the site from the other hand without previous enrollment of such site.

Figure 10:
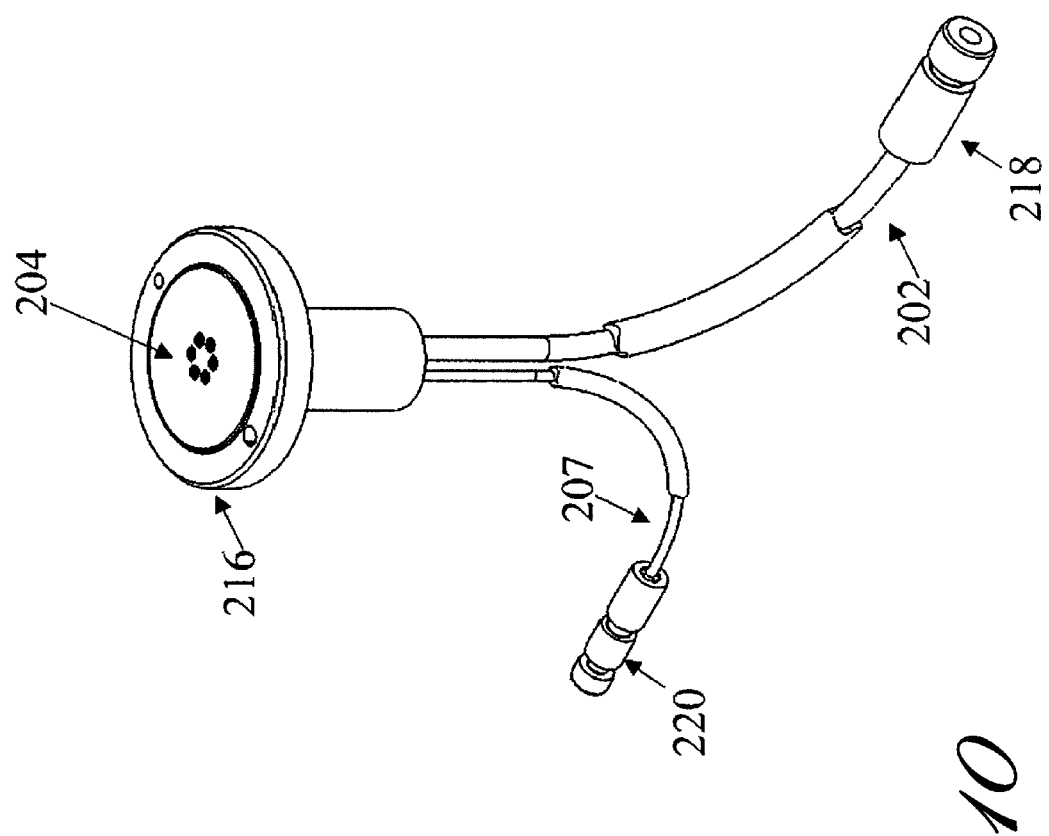
FIG. 10 is a perspective view of elements of an example tissue sampling subsystem.

As illustrated in FIG. 6, the sampling subsystem 200 introduces radiation generated by the illumination subsystem 100 to the sample and collects portions of the radiation that were not absorbed by the sample and sends that radiation to a spectrometer subsystem 300 for measurement. FIGS. 10 through 14 depict elements of preferred embodiments of the sampling subsystem 200. Referring to FIG. 10, the sampling subsystem 200 has an optical input 202, a sampling surface 204 which forms an interface 206 that interrogates the sample and an optical output 207. In a preferred subsystem, a device that thermostats the sampling subsystem/sample interface is included. In other embodiments, an index matching fluid can be used to improve the optical interface between the sample and sampling subsystem. See, e.g. U.S. Pat. No. 6,152,876 to Robinson et al., incorporated herein by reference. In some measurement applications, the index matching fluid can be considered an interferent that warrants application of a mitigation method as described in co-pending U.S. application Ser. No. 11/305,964.

Figure 11:
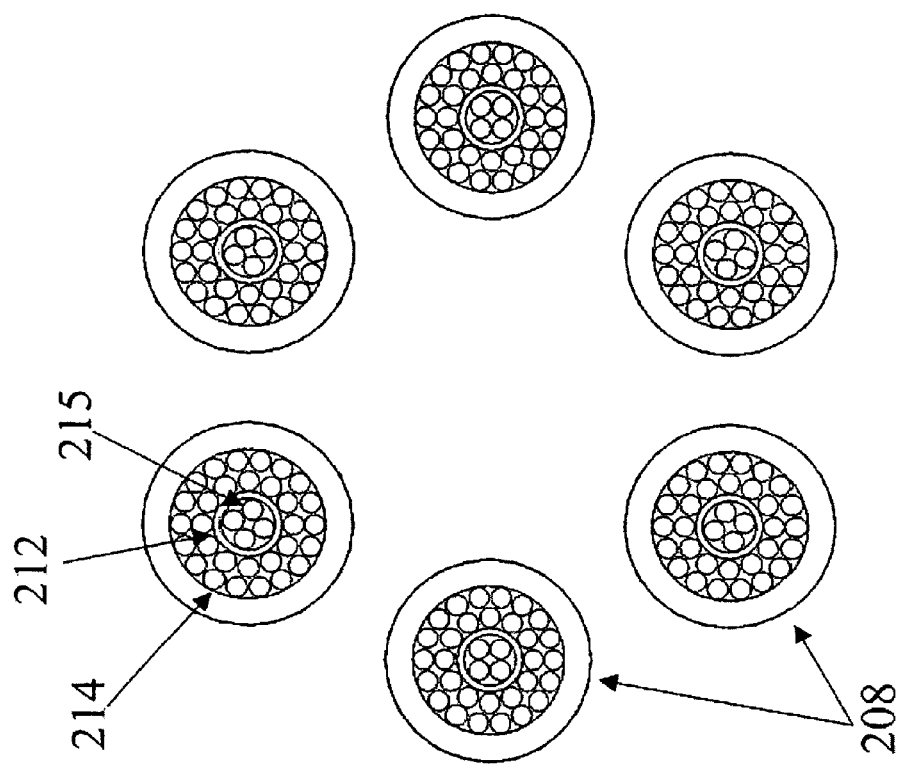
FIG. 11 is a plan view of the sampling surface of the tissue sampling subsystem, showing an example arrangement of input and output optical fiber ends.

The optical input 202 of the sampling subsystem 200 receives radiation from the illumination subsystem 100 (e.g., light exiting a light pipe or other means for coupling light) and transfers that radiation to the interface 206. As an example, the optical input can comprise a bundle of optical fibers that are arranged in a geometric pattern that collects an appropriate amount of light from the illumination subsystem. The sampling head 216 includes a sampling surface 204, polished flat to encourage formation of a good interface with the sample and prevent accumulation of interferents on the sampling head surface. FIG. 11 depicts one example arrangement. The plan view depicts the ends of the input and output fibers in a geometry at the sampling surface including six clusters 208 arranged in a circular pattern. Each cluster includes four central output fibers 212, which collect diffusely reflected light from the sample. Around each grouping of four central output fibers 212 is a cylinder of material 215, which ensures about a 100 µm gap between the edges of the central output fibers 212 and the inner ring of input fibers 214. The 100 µm gap can be important to measuring certain analytes. As shown in FIG. 11, two concentric rings of input fibers 214 can be arranged around the cylinder of material 215. As shown in one example embodiment, 32 input fibers surround four output fibers.

Figure 12:
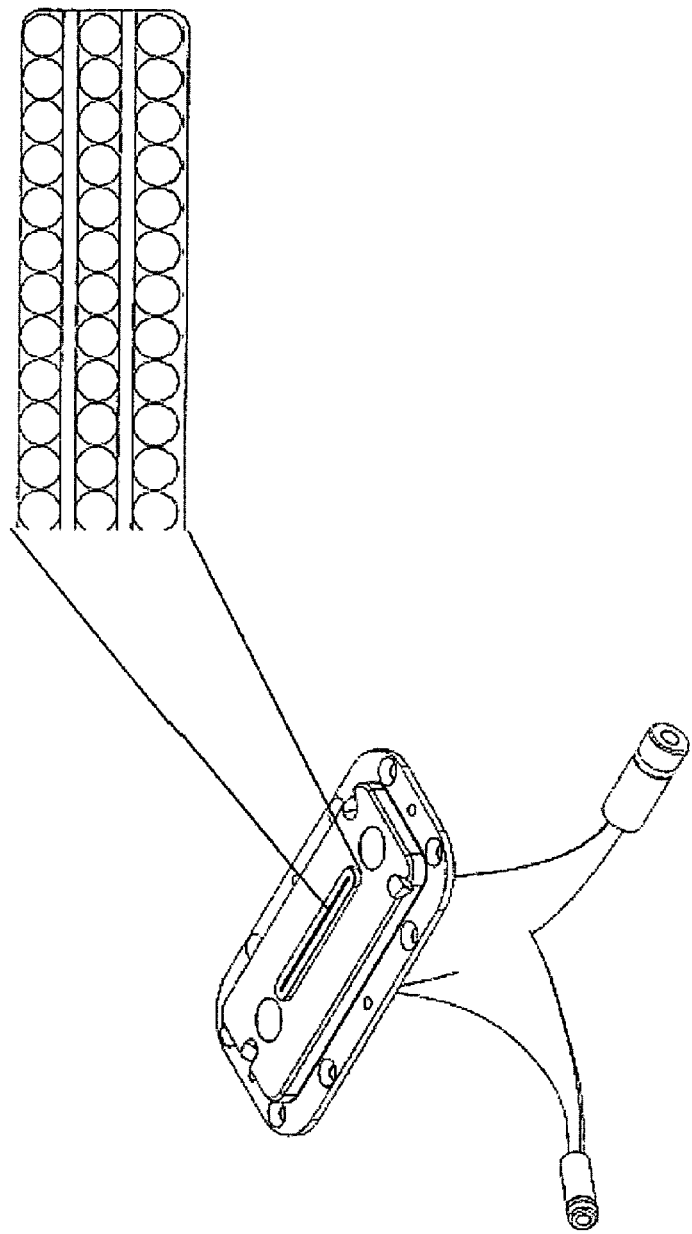
FIG. 12 is an alternative embodiment of a sampling surface of a tissue sampling subsystem.

FIG. 12 demonstrates an alternative to cluster geometries for the sampling subsystem. In this embodiment, the illumination and collection fiber optics are arranged in a linear geometry. Each row can be either for illumination or light collection and can be of any length suitable to achieve sufficient signal to noise. In addition, the number of rows can be 2 or more in order to control the physical area covered by the sampling subsystem. The total number of potential illumination fibers can depend on the physical size of emissive area of the light source and the diameter of each fiber. Multiple light sources can be used in the illumination subsystem 100 to increase the number of illumination fibers. The number of collection fibers can depend on the area of the interface to the spectrometer subsystem 300. If the number of collection fibers results in an area larger than the spectrometer subsystem 300 interface allows, a light pipe or other homogenizer followed by an aperture can be used to reduce the size of the output area of the sampling subsystem. The light pipe or other homogenizer can encourage that each collection fiber contributes substantially equally to the light that passes through the aperture.

Figure 13:
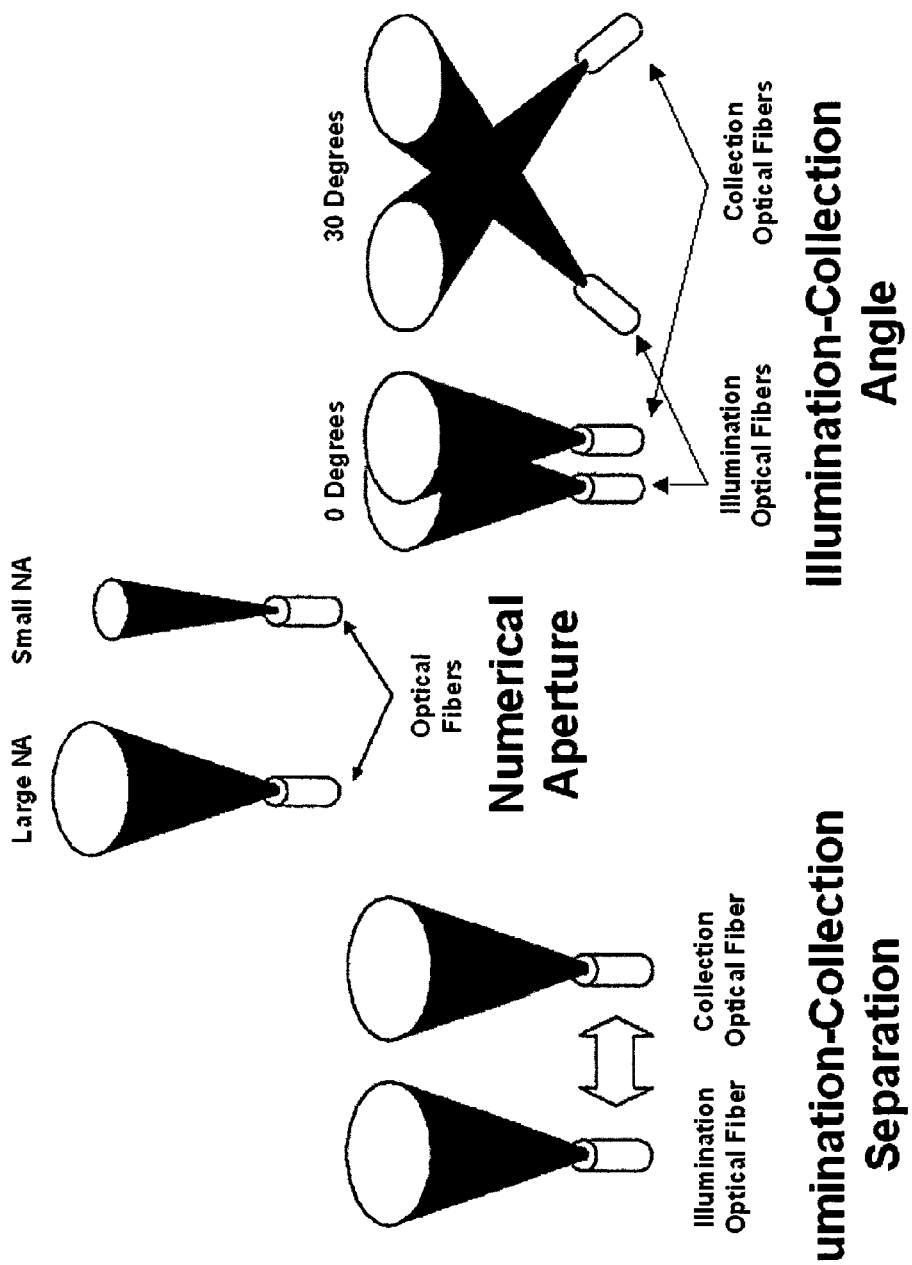
FIG. 13 depicts various aspects of a sampler orientation.
Figure 14:
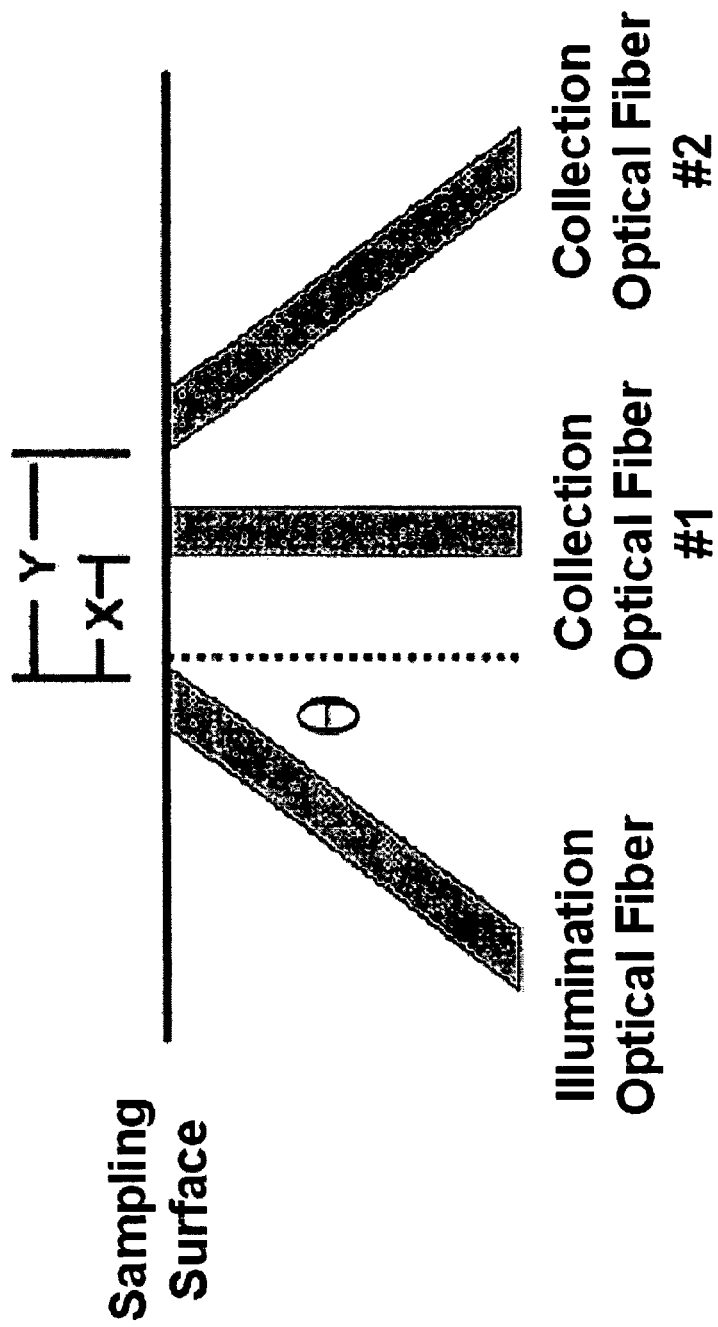
FIG. 14 is a diagramed view of a two-channel sampling subsystem.

The sampling subsystem can use one or more channels, where a channel refers to a specific orientation of the illumination and collection fibers. An orientation is comprised of the angle of the illumination fiber or fibers, the angle of the collection fiber or fibers, the numerical aperture of the illumination fiber or fibers, the numerical aperture of the collection fiber or fibers, and the separation distance between the illumination and collection fiber or fibers. FIG. 13 is a diagram of parameters that form an orientation. Multiple channels can be used in conjunction, either simultaneously or serially, to improve analyte measurements. FIG. 14 is a diagram of a two channel sampling subsystem. Each channel provides a measurement of the sample from a different perspective. The second perspective can help to provide additional spectroscopic information that helps to decouple the signals due to scattering, absorption, and topical interferents on the skin surface. Referring to FIG. 14, the group of fibers (1 source, 1 receiver #1, and 1 receiver #2 in this example) can be replicated 1 to N times in order to increase the sampler area and improve optical efficiency. Each of the fibers can have a different numerical aperture and angle (θ). The distances between fibers, X and Y, determine the source-receiver separation. Furthermore, an additional source channel can be added that creates a 4-channel sampling subsystem. Those skilled in the art will appreciate many variations contemplated by the present invention and illustrated by the examples discussed.

In addition to the use of optical fibers, the sampling subsystem can use a non-fiber based arrangement that places a pattern of input and output areas on the sample surface. In some embodiments, the input and output elements of the sampling subsystem can be comprised of a lens system. In a preferred embodiment, the input element and output element comprise a single lens system that is utilized for both input of light from the energy source and the collection of both specularly and diffusely reflected light from the sample. Alternatively, the input element and output element can comprise two lens systems, placed on opposing sides of an analyte-containing sample, wherein light from the energy source is transmitted to the input element and onto the sample, and light transmitted through the analyte-containing sample then passes through the output element to the spectrum analyzer. Proper masking of the non-fiber based tissue sampling interface ensures that the input light travels a minimum distance in the tissue and contains valid attribute information.

The spectrometer subsystem 300 can be comprised of a variety of different technologies and approaches including interferometers (Michelson, mock, Sagnac) and dispersive spectrometers (diffraction gratings, prisms). As demonstrated in FIGS. 6 and 7, any of these spectrometer types can be placed before or after the sampling subsystem. In some embodiments of the orientation shown in FIG. 7 the illumination 1000 and spectrometer 300 subsystems can be combined. In these embodiments, the combined illumination-spectrometer subsystem's fundamental building blocks are one or more sources of specific wavelengths of light and some means to combine them. One example embodiment comprises multiple, individually addressed, sources (e.g. laser diodes, Vertical Cavity Emitting Laser (VCSEL), Quantum Dots, and/or Light Emitting Diodes (LEDs)) that illuminate the tissue directly. The tissue then serves as the means to combine the various wavelengths. In other embodiments, the light emitted by the individual sources is combined with a dedicated device such as an integrating chamber, light pipe or homogenizer, or a dispersive element (prism or grating). This device combines the multiple sources into a single output beam. Alternatively, a single, tunable narrow band source (e.g. a vertical cavity surface emitting laser, tunable diode or diode laser) can be used by scanning through its range of tunable wavelengths.

In such embodiments, each source can be modulated in time at a frequency that differs from the other sources in the subsystem. The modulation process is easily accomplished with semiconductor light sources that can be rapidly turned on and off at a variety of frequencies. The combined beam, that contains the various wavelengths that have been uniquely modulated, is equivalent in purpose to the beam that would be obtained from a single broadband source that is subsequently modulated or dispersed by a dedicated spectrometer subsystem. The combined beam is then introduced to the tissue sampling subsystem and ultimately the detector in the data acquisition subsystem. The data acquisition subsystem then decodes the signal into its individual wavelength components via an appropriate technique such as a Fourier or Hadamard transform.

New characteristics and advantages of the invention covered by this document have been set forth in the foregoing description. It will be understood, however, that this disclosure is, in many respects, only illustrative. Changes can be made in details, particularly in matters of shape, size, and arrangement of parts or steps, without exceeding the scope of the invention. The scope of the invention is, of course, defined in the language in which the appended claims are expressed.

Methods for Determining Alcohol Concentration from the Spectroscopic Signal

The Beer-Lambert law is commonly invoked in absorption spectroscopy to elucidate the relationship between the measured signal and the property of interest (alcohol concentration). For a sample containing a single absorbing analyte that is spectroscopically measured at a single wavelength, the Beer-Lambert Law can be expressed as:

$$A_\lambda = \epsilon_\lambda l c \quad \text{(eq. 1)}$$

where $A_\lambda$ is the absorption of the sample at wavelength $\lambda$, $\epsilon_\lambda$ is the absorptivity of the single analyte in the sample at wavelength $\lambda$, l is the pathlength that the light travels through the sample, and c is the concentration of the analyte. As such, the Beer-Lambert Law states that a linear relationship between the absorbance of the sample and the concentration of the analyte in the sample. In order to determine the concentration of the analyte in practice, $\epsilon_\lambda$ and l must be known quantities such that upon experimental measurement of $A_\lambda$, the concentration (c) is the only remaining unknown.

The Beer-Lambert Law can be extended to samples containing more than one analyte; however, additional wavelengths must be measured in order to determine the property of interest. For example, a sample containing 2 analytes must be measured at two wavelengths according to the following equations:

$$A_{\lambda 1} = \epsilon_{\alpha \lambda 1} l c_\alpha + \epsilon_{\beta \lambda 1} l c_\beta$$

and $$A_{\lambda 2} = \epsilon_{\alpha \lambda 2} l c_\alpha + \epsilon_{\beta \lambda 2} l c_\beta \quad \text{(eqs. 2 and 3)}$$

where $\alpha$ and $\beta$ represent the 2 analytes and $\lambda 1$ and $\lambda 2$ are the two measured wavelengths. From a mathematical perspective, the number of unknowns (concentrations) in the system of equations can never exceed the number of equations, thus necessitating the measurement of additional wavelengths (to add more equations) and complete characterization of the sample (all $\epsilon$ terms must be separately determined and the pathlength l must be known). Clearly, this places a significant burden on the direct application of the Beer-Lambert Law and similar direct solution methods such as Classical Least Squares (CLS) as all analytes present in the sample must be identified and their absorptivities determined.

Spectral measurements of complex media, such as human tissue, can be comprised of many overlapping spectral signatures from a large number of chemical analytes. While feasible in some situations depending on the measurement objectives, the Beer-Lambert/CLS class of approaches can be difficult to implement due to the large number of variables. In such cases, alternative multivariate analysis methods can be used to decouple the signal of the analyte of interest from the signals of other analytes in the system (interferents). Partial Least Squares (PLS) regression is a well established multivariate analysis method that has been applied quantitative analysis of spectroscopic measurements and will be used for demonstrative purposes for the remainder of the disclosure. However, other multivariate analysis methods such as Principal Components Regression (PCR), Ridge Regression, Multiple Linear Regression (MLR) and Neural Networks are equally suitable for the present invention. One skilled in the art will recognize that other methods of similar functionality are also applicable.

In PLS regression, a set of spectroscopic calibration measurements is acquired where each has a corresponding reference value for the property of interest (e.g. blood alcohol concentration). The calibration spectral data are then decomposed into a series of factors (spectral shapes that are sometimes called loading vectors or latent variables) and scores (the magnitude of the projection of each spectrum onto a given factor) such that the squared covariance between the reference values and the scores on each successive PLS loading vector is maximized. The scores of the calibration spectra are then regressed onto the reference values in a multiple linear regression (MLR) step in order to calculate a set of spectral weights (one weight per wavenumber in the spectra) that minimizes the analyte measurement error of the calibration measurements in a least-squares sense. These spectral weights are called the regression vector of the calibration model. Once the calibration model is established, subsequent measurements are obtained by calculating the vector dot product of the regression vector and each measured spectrum.

The primary advantage of PLS and similar methods (commonly referred to as indirect methods) is that the $\epsilon$ terms in the Beer-Lambert Law (and thus the complete composition of the sample) do not need to be known. Furthermore, inverse methods tend to be more robust at dealing with nonlinearities in the spectral measurement such as those caused by instrumental drift, light scattering, environmental noise, and chemical interactions.

Figure 15:
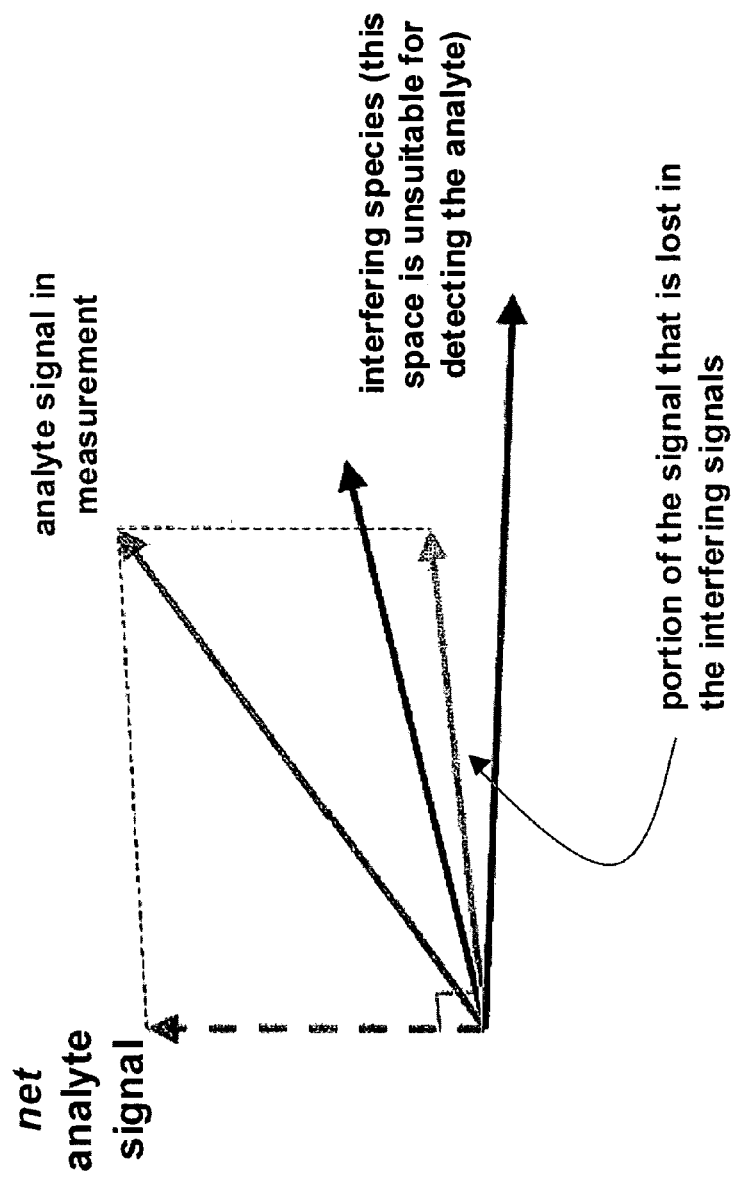
FIG. 15 is a diagram of the net analyte signal (NAS) for a 3 component system.

Functionally, the goal of the multivariate calibration (PLS or otherwise) in the present invention is to determine the part of the spectroscopic signal of alcohol that is effectively orthogonal (contravariant) to the spectra of all interferents in the sample. This part of the signal is referred to as the net attribute signal and can be calculated using the regression vector (b) described above using equation 4. If there are no interfering species, the net attribute spectrum is equal to the pure spectrum of alcohol. If interfering species with similar spectra to the attribute are present, the net attribute signal will be reduced relative to the entire spectrum. The concept of net attribute signal for a three-analyte system is depicted graphically in FIG. 15.

$$NAS = \frac{\hat{b}}{\|\hat{b}\|_2^2} \quad \text{(eq. 4)}$$

In other embodiments of the present invention, a hybrid calibration model can be used to measure the alcohol concentrations of subject spectra. The term hybrid model denotes that a partial least squares (PLS) calibration model was developed using a combination of in vitro and in vivo spectral data. The in vitro portion of the data can comprise a 0.1 mm pathlength transmission spectrum of 500 mg/dL alcohol in water measured using a non-invasive measurement system configured for transmission measurements. The transmission spectrum can be ratioed to a 0.1 mm pathlength transmission spectrum of water, converted to absorbance, and normalized to unit pathlength and concentration.

Figure 16:
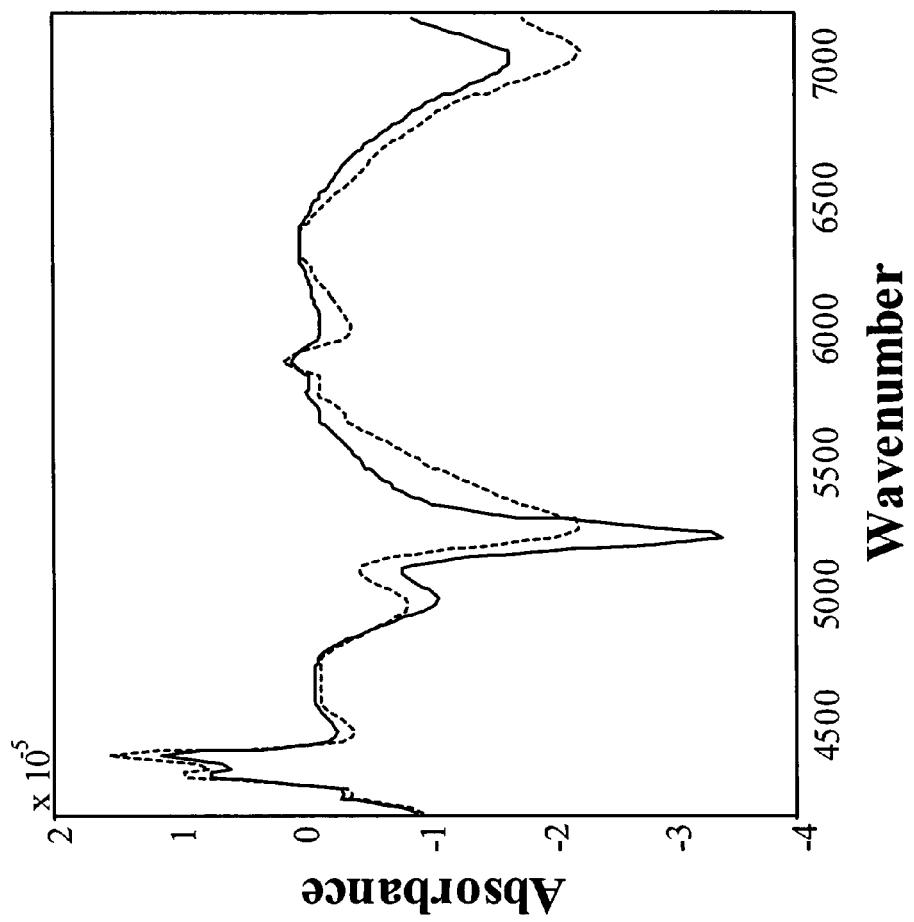
FIG. 16 is a diagram of the near infrared absorptivity of alcohol before and after tissue pathlength correction.

Light propagation through tissue is a complex function of the diffuse reflectance optical tissue sampler design, physiological variables, and wavenumber. Consequently, the pathlength of light through tissue has a wavenumber dependence that is not encountered in scatter-free transmission measurements. In order to account for the wavenumber dependence, the interaction of the optical tissue sampler with the scattering properties of human tissue can be modeled via Monte-Carlo simulation using a commercial optical ray-tracing software package (e.g., TracePro). Using the resulting model of the photon-tissue interactions, an estimate of the effective pathlength of light through the dermis and subcutaneous tissue layers as a function of wavenumber can be generated. The effective pathlength ($l_{eff}$) is defined as $$l_{eff}(v) = \frac{\sum_{i=1}^{N} l_i \exp(-\mu_a(v)l_i)}{\sum_{i=1}^{N} l_i} \quad \text{(eq. 5)}$$

where v is wavenumber, $l_i$ is the pathlength traversed by the $i^{th}$ ray in the Monte Carlo simulation [mm], N is the total number of rays in the simulation, and $\mu_a$ is the (wavenumber-dependent) absorption coefficient [$mm^{-1}$]. Due to its large absorption in vivo, water is the only analyte that has a significant effect on the effective pathlength. Therefore, for the purposes of the effective pathlength calculation, the absorption coefficients used were those of water at physiological concentrations. The alcohol absorbance spectrum (as measured in transmission) was then scaled by the computed path function to form a corrected alcohol spectrum representative of the wavenumber dependent pathlength measured by the diffuse reflectance optical sampler. FIG. 16 shows the alcohol absorbance spectrum before and after correction by the path function. This corrected spectrum formed the base spectrum for the mathematical addition of alcohol to the calibration spectra.

Figure 17:
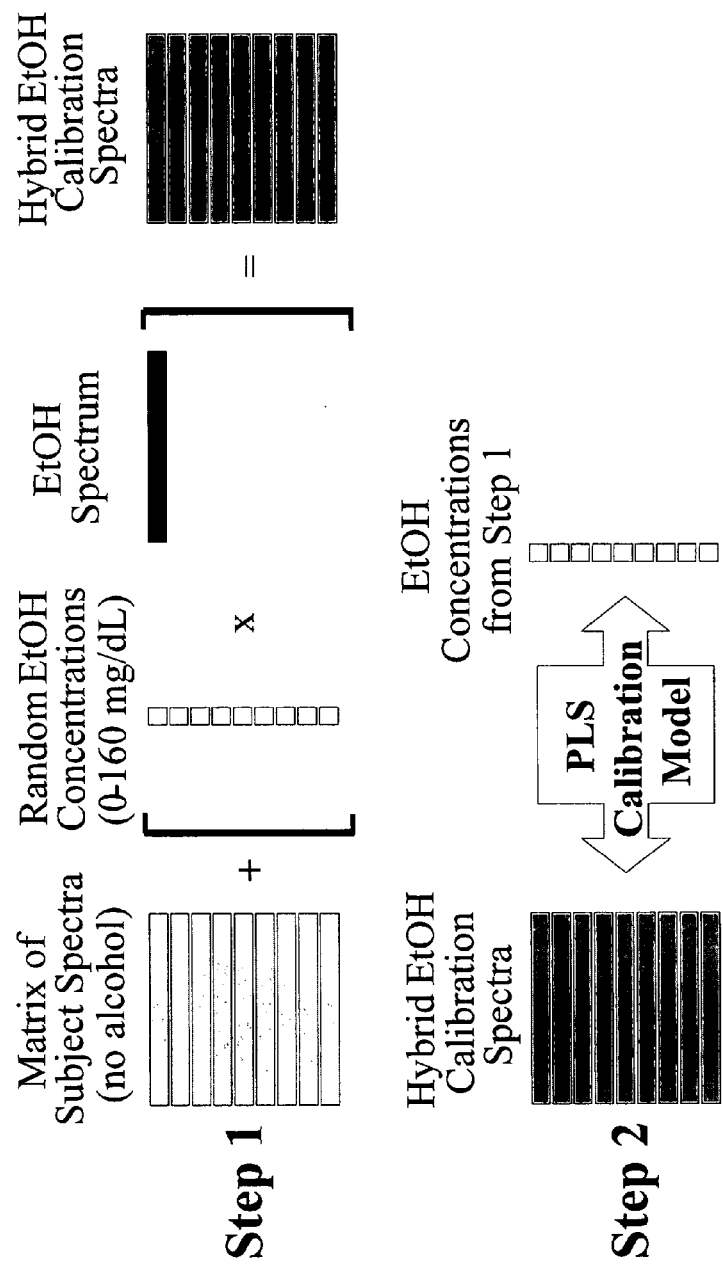
FIG. 17 is a schematic representation of the hybrid calibration formation process.

The in vivo data comprised noninvasive tissue spectra collected from persons who had not consumed alcohol. A hybrid model was formed by adding the alcohol pure component spectrum, weighted by various alcohol "concentrations" (ranging from 0 to 160 mg/dL), to the noninvasive tissue spectral data. The PLS calibration model was built by regressing the synthetic alcohol concentrations on the hybrid spectral data. FIG. 17 is a schematic representation of the hybrid calibration formation process. The hybrid calibration in this work used approximately 1500 non-invasive tissue spectra that were collected from 133 subjects over three months.

The use of hybrid calibration models, rather than calibration models built from spectra acquired from subjects who have consumed alcohol, can provide advantages. The hybrid modeling process makes it possible to generate calibration spectra that contain higher concentrations (up to 160 mg/dL in one example) of alcohol than would be considered safe for consumption in a human subject study (120 mg/dL is generally considered a safe upper limit). The result can be a stronger calibration with a wider range of analyte concentrations that is able to more accurately measure higher alcohol concentrations. This can be important because alcohol concentrations observed in the field can be more than double the maximum safe dosage in a clinical research setting. The hybrid calibration process also allows the prevention of correlations between alcohol and the spectral interferents naturally or artificially present in or on the surface of the tissue, thus generating a regression vector with a larger net attribute signal. For example, the random addition of alcohol signal to the calibration spectra prevents alcohol concentration from being correlated with water concentration. Thus, the hybrid approach reduces the possibility that the measurement could spuriously track changes in tissue water content instead of alcohol concentration.

Alternative calibration strategies can be used in place of, or in conjunction with, the above described methods. For example, in some embodiments biometric enrollment information is acquired from each person who is authorized to use a given piece of machinery or vehicle. In such cases, the enrollment measurements can also be used to improve the accuracy and precision of the alcohol or substance of abuse measurement. In this scenario, the calibration spectra are mean-centered by subject (all spectra from a subject are located, the mean of those spectra is subtracted from each, and the "mean centered" spectra are returned to the spectral set). In this manner, the majority of inter-subject spectral differences caused by variations in physiology are removed from the calibration measurements and the range of spectral interferents correspondingly reduced. The centered spectra and associated analyte reference values (blood alcohol concentrations) are then presented to a multivariate analysis method such as partial least squares regression. This process is referred to as generating an "enrolled", "generic", or "tailored" calibration. Additional details on this approach are described in U.S. Pat. No. 6,157,041, entitled "Methods and Apparatus for Tailoring Spectroscopic Calibration Models," the disclosure of which is incorporated by reference.

In practice, once a future, post calibration, subject is enrolled on a noninvasive device their enrollment spectrum can be subtracted from subsequent measurements prior to determining the alcohol or substance of abuse concentration using the generic calibration model. Similar to the mean-centering by subject operation of the calibration spectra, the subtraction of the enrollment spectrum removes the average spectroscopic signature of the subject while preserving the signal of the analyte of interest (alcohol or substance of abuse). In some embodiments, significant performance advantages can be realized relative to the use of a non-generic calibration method.

Once formed, a calibration (generic or otherwise) should remain stable and produce accurate attribute predictions over a desired period of time. This process is referred to as calibration maintenance and can comprise multiple methods that can be used individually or in conjunction. The first method is to create the calibration in a manner that inherently makes it robust. Several different types of instrumental and environmental variation can affect the measurement capability of a calibration model. It is possible and desirable to reduce the magnitude of the effect of instrumental and environmental variation by incorporating this variation into the calibration model.

It is difficult, however, to span the entire possible range of instrument states during the calibration period. System perturbations can result in the instrument being operated outside the space of the calibration model. Examples of potentially problematic instrument and environmental variation include, but are not limited to changes in the levels of environmental interferents such as water vapor or $CO_2$ gas, changes in the alignment of the instrument's optical components, fluctuations in the output power of the instrument's illumination system, and changes in the spatial and angular distribution of the light output by the instrument's illumination system. Measurements made while the instrument is in an inadequately modeled state can exhibit measurement errors. In the case of in vivo optical measurements of analyte properties, these types of errors can result in erroneous measurements that degrade the utility of the system. Therefore it is often advantageous to use additional calibration maintenance techniques during the life of the instrument in order to continually verify and correct for the instrument's status.

Calibration maintenance techniques are discussed in commonly assigned U.S. patent application Ser. No. 09/832,608, "Optically Similar Reference Samples and Related Methods for Multivariate Calibration Models Used in Optical Spectroscopy," and U.S. patent application Ser. No. 10/281,576, "Optically Similar Reference Samples," and U.S. patent application Ser. No. 10/733,195, "Adaptive Compensation for Measurement Distortions in Spectroscopy," each of which is incorporated herein by reference. These methods use an environmentally inert non-tissue sample, such as an integrating sphere, that optionally contains the attribute of interest, in order to monitor the instrument over time. The sample can be incorporated into the optical path of the instrument or interface with the sampling subsystem in a manner similar to that of tissue measurements. The sample can be used in transmission or in reflectance and can contain stable spectral features or contribute no spectral features of its own. The material can be a solid, liquid, or gel material as long as its spectrum is stable or predicable over time. Any unexplained change in the spectra acquired from the sample over time indicate that the instrument has undergone a perturbation or drift due to environmental effects. The spectral change can then be used to correct subsequent tissue measurements in humans in order to ensure and accurate attribute measurement.

Once a calibration is formed, it is desirable to transfer the calibration to existing and future instruments. This process is commonly referred to as calibration transfer. While not required, calibration transfer prevents the need for a calibration to be built on each system that is manufactured. This represents a significant time and cost savings that could result in the difference between success or failure of a commercial product. Calibration transfer arises from the fact that optical and electronic components vary from unit to unit which, in aggregate, results in differences in the spectra obtained from multiple instruments. For example, two light sources can have different color temperatures thereby resulting in a different light distribution for the two sources. The responsivity of two detectors can also differ significantly, which can result in additional spectral differences.

Similar to calibration maintenance, multiple methods can be used in order to effectively achieve calibration transfer. The first method is to build the calibration with multiple instruments. The presence of multiple instruments allows the spectral variation associated with instrument differences to be determined and made effectively orthogonal to the attribute signal during the calibration formation process. While this does approach reduces the net attribute signal, it can be an effective means of calibration transfer.

Additional calibration transfer methods involve explicitly determining the difference in the spectral signature of a system relative to those used to build the calibration. In this case, the spectral difference can then be used to correct a spectral measurement prior to attribute prediction on a system or it can be used to correct the predicted attribute value directly. The spectral signature specific to an instrument can be determined from the relative difference in spectra of a stable sample acquired from the system of interest and those used to build the calibration. Many suitable approaches and algorithms for effective calibration transfer are known in the art; some of which are summarized in "Standardisation and Calibration Transfer for Near Infrared Instruments: a Review", by Tom Fearn in the Journal of Near Infrared Spectroscopy, vol. 8, pp. 229-244 (2001). Note that these approaches and algorithms are equally suited to other spectroscopic techniques such as Raman measurements. The samples described in the calibration maintenance section can also be applicable to calibration transfer. See, e.g. U.S. Pat. No. 6,441,388, incorporated herein by reference.

Methods for Determining Biometric Verification/Identification from Spectroscopic Signal Biometric identification describes the process of using one or more physical or behavioral features to identify a person or other biological entity. There are two common biometric modes: identification and verification. Biometric identification attempts to answer the question of, "do I know you?" The biometric measurement device collects a set of biometric data from a target individual. From this information alone it assesses whether the person was previously enrolled in the biometric system. Systems that perform the biometric identification task, such as the FBI's Automatic Fingerprint Identification System (AFIS), are generally very expensive (several million dollars or more) and require many minutes to detect a match between an unknown sample and a large database containing hundreds of thousands or millions of entries. In biometric verification the relevant question is, "are you who you say you are?" This mode is used in cases where an individual makes a claim of identity using a code, magnetic card, or other means, and the device uses the biometric data to confirm the identity of the person by comparing the target biometric data with the enrolled data that corresponds with the purported identity. Interlock methods for preventing operation of machinery or vehicles by intoxicated or impaired persons can use either biometric mode.

There also exists at least one variant between these two modes that is also suitable for use in an interlock method. This variant occurs in the case where a small number of individuals are contained in the enrolled database and the biometric application requires the determination of only whether a target individual is among the enrolled set. In this case, the exact identity of the individual is not required and thus the task is somewhat different (and often easier) than the identification task described above. This variant might be useful in applications where the biometric system is used in machinery or vehicle interlock methods where the prospective operator must be both part of the authorized group and sober but their specific identity is not required. The term "identity characteristic" includes all of the above modes, variants, and combinations or variations thereof.

There are three major data elements associated with a biometric measurement: calibration, enrollment, and target spectral data. The calibration data are used to establish spectral features that are important for biometric determinations. This set of data consists of series of spectroscopic tissue measurements that are collected from an individual or individuals of known identity. Preferably, these data are collected over a period of time and a set of conditions such that multiple spectra are collected on each individual while they span nearly the full range of physiological states that a person is expected to go through. In addition, the instrument or instruments used for spectral collection generally should also span the full range of instrumental and environmental effects that it or sister instruments are likely to see in actual use. These calibration data are then analyzed in such a way as to establish spectral wavelengths or "factors" (i.e. linear combinations of wavelengths or spectral shapes) that are sensitive to between-person spectral differences while minimizing sensitivity to within-person, instrumental (both within- and between-instruments), and environmental effects. These wavelengths or factors are then used subsequently to perform the biometric determination tasks.

The second major set of spectral data used for biometric determinations is the enrollment spectral data. The purpose of the enrollment spectra for a given subject or individual is to generate a "representation" of that subject's unique spectroscopic characteristics. Enrollment spectra are collected from individuals who are authorized or otherwise required to be recognized by the biometric system. Each enrollment spectrum can be collected over a period of seconds or minutes. Two or more enrollment measurements can be collected from the individual to ensure similarity between the measurements and rule out one or more measurements if artifacts are detected. If one or more measurements are discarded, additional enrollment spectra can be collected. The enrollment measurements for a given subject can be averaged together, otherwise combined, or stored separately. In any case, the data are stored in an enrollment database. In some cases, each set of enrollment data are linked with an identifier (e.g. a password or key code) for the persons on whom the spectra were measured. In the case of an identification task, the identifier can be used for record keeping purposes of who accessed the biometric system at which times. For a verification task, the identifier is used to extract the proper set of enrollment data against which verification is performed.

The third and final major set of data used for the biometric system is the spectral data collected when a person attempts to use the biometric system for identification or verification. These data are referred to as target spectra. They are compared to the measurements stored in the enrollment database (or subset of the database in the case of identity verification) using the classification wavelengths or factors obtained from the calibration set. In the case of biometric identification, the system compares the target spectrum to all of the enrollment spectra and reports a match if one or more of the enrolled individual's data is sufficiently similar to the target spectrum. If more than one enrolled individual matches the target, then either all of the matching individuals can be reported, or the best match can be reported as the identified person. In the case of biometric verification, the target spectrum is accompanied by an asserted identity that is collected using a magnetic card, a typed user name or identifier, a transponder, a signal from another biometric system, or other means. The asserted identity is then used to retrieve the corresponding set of spectral data from the enrollment database, against which the biometric similarity determination is made and the identity verified or denied. If the similarity is inadequate, then the biometric determination is cancelled and a new target measurement may be attempted.

In one method of verification, principle component analysis is applied to the calibration data to generate spectral factors. These factors are then applied to the spectral difference taken between a target spectrum and an enrollment spectrum to generate Mahalanobis distance and spectral residual magnitude values as similarity metrics. Identify is verified only if the aforementioned distance and magnitude are less than a predetermined threshold set for each. Similarly, in a preferred method for biometric identification, the Mahalanobis distance and spectral residual magnitude are calculated for the target spectrum relative each of the database spectra. The identify of the person providing the test spectrum is established as the person or persons associated with the database measurement that gave the smallest Mahalanobis distance and spectral residual magnitude that is less than a predetermined threshold set for each.

In a preferred method, the identification or verification task is implemented when a person seeks to perform an operation for which there are a limited number of people authorized (e.g., perform a spectroscopic measurement, achieve control over an interlocked vehicle or piece of machinery, pass through an immigration checkpoint, etc.). The person's spectral data is used for identification or verification of the person's identity. In this preferred method, the person initially enrolls in the system by collecting one or more representative tissue spectra. If two or more spectra are collected during the enrollment, then these spectra be checked for consistency and recorded only if they are sufficiently similar, limiting the possibility of a sample artifact corrupting the enrollment data. For a verification implementation, an identifier such as a PIN code, magnetic card number, username, badge, voice pattern, other biometric, or some other identifier can also be collected and associated with the confirmed enrollment spectrum or spectra.

In subsequent use, biometric identification would take place by collecting a spectrum from a person attempting to gain authorization. This spectrum would then be compared to the spectra in the enrolled authorization database and an identification made if the match to an authorized database entry was better than a predetermined threshold. The verification task is similar, but would require that the person present the identifier in addition to a collected spectrum. The identifier would then be used to select a particular enrollment database spectrum and authorization would be granted if the current spectrum was sufficiently similar to the selected enrollment spectrum. If the biometric task is associated with an operation for which only a single person is authorized, then the verification task and identification task are the same and both simplify to an assurance that the sole authorized individual is attempting the operation without the need for a separate identifier.

The biometric measurement, regardless of mode, can be performed in a variety of ways including linear discriminant analysis, quadratic discriminant analysis, K-nearest neighbors, neural networks, and other multivariate analysis techniques or classification techniques. Some of these methods rely upon establishing the underlying spectral shapes (factors, loading vectors, eigenvectors, latent variables, etc.) in the intra-person calibration database, and then using standard outlier methodologies (spectral F ratios, Mahalanobis distances, Euclidean distances, etc.) to determine the consistency of an incoming measurement with the enrollment database. The underlying spectral shapes can be generated by multiple means as disclosed herein.

First, the underlying spectral shapes can be generated based upon simple spectral decompositions (eigen analysis, Fourier analysis, etc.) of the calibration data. The second method of generating underlying spectral shapes relates to the development of a generic model as described in U.S. Pat. No. 6,157,041, entitled "Methods and Apparatus for Tailoring Spectroscopic Calibration Models," the disclosure of which is incorporated by reference. In this application, the underlying spectral shapes are generated through a calibration procedure performed on intra-person spectral features. The underlying spectral shapes can be generated by the development of a calibration based upon simulated constituent variation. The simulated constituent variation can model the variation introduced by real physiological or environmental or instrumental variation or can be simply be an artificial spectroscopic variation. It is recognized that other means of determining underlying shapes would be applicable to the identification and verification methods of the present invention. These methods can be used either in conjunction with, or in lieu of the aforementioned techniques.

Methods for Preventing Machinery or Vehicle Operation

The final component of an effective machinery or vehicle interlock is a means for preventing or controlling its operation. In the case of vehicle interlocks, the ignition system is widely recognized as a feasible means for preventing the starting of the motor. However other types of interlocks can also be suitable, and might be advantageous in some situations. For example, in the case of a failed alcohol test, a transmission interlock would allow the motor to be started and accessories (e.g. the radio, phone) to be used while the operator finds other means of travel. Brake, steering wheel, engine control system, or computer locks are also potential means for preventing operation. The signal required to enable or disable the vehicle or machinery can be wireless or wired as deemed appropriate for the application. Furthermore, in some embodiments, wireless communication can also be used to report the measurement results of the interlock or the operational status of the interlock device to monitoring or law enforcement facilities. One skilled in the art will appreciate the wide variety of machinery and vehicle systems that could feasibly incorporate or function as an interlock or control.

Generally, the present invention allows many types of control of the operation of equipment. Specific modes of operation (e.g., ignition disable, transmission disable, accessory enable, event reporting) can depend on the analyte property (e.g., alcohol concentration) and the identity characteristic (e.g., some operators may have access to limited operation, event reporting might require specific individual identification); any specification of such equipment control is termed an "equipment operation parameter."

As mentioned above, the alcohol interlock device of the present invention can be configured to allow the car to start prior to alcohol or biometric determinations, or independently of one or both determinations. The interlock device can then disable driving operation via control of the vehicle's transmission, braking system, or other suitable secondary methods. This scheme also allows for interlock systems which require significant system power during operation. It is recognized that some of the proposed instrumentation systems may require high power light sources and/or reasonably lengthy operation periods prior to completing a driver's biometric authentication and alcohol test. By configuring the invention to operate after a vehicle has been started, significantly more system power is available to enable the use of more sophisticated and higher power instrumentation.

Figure 18:
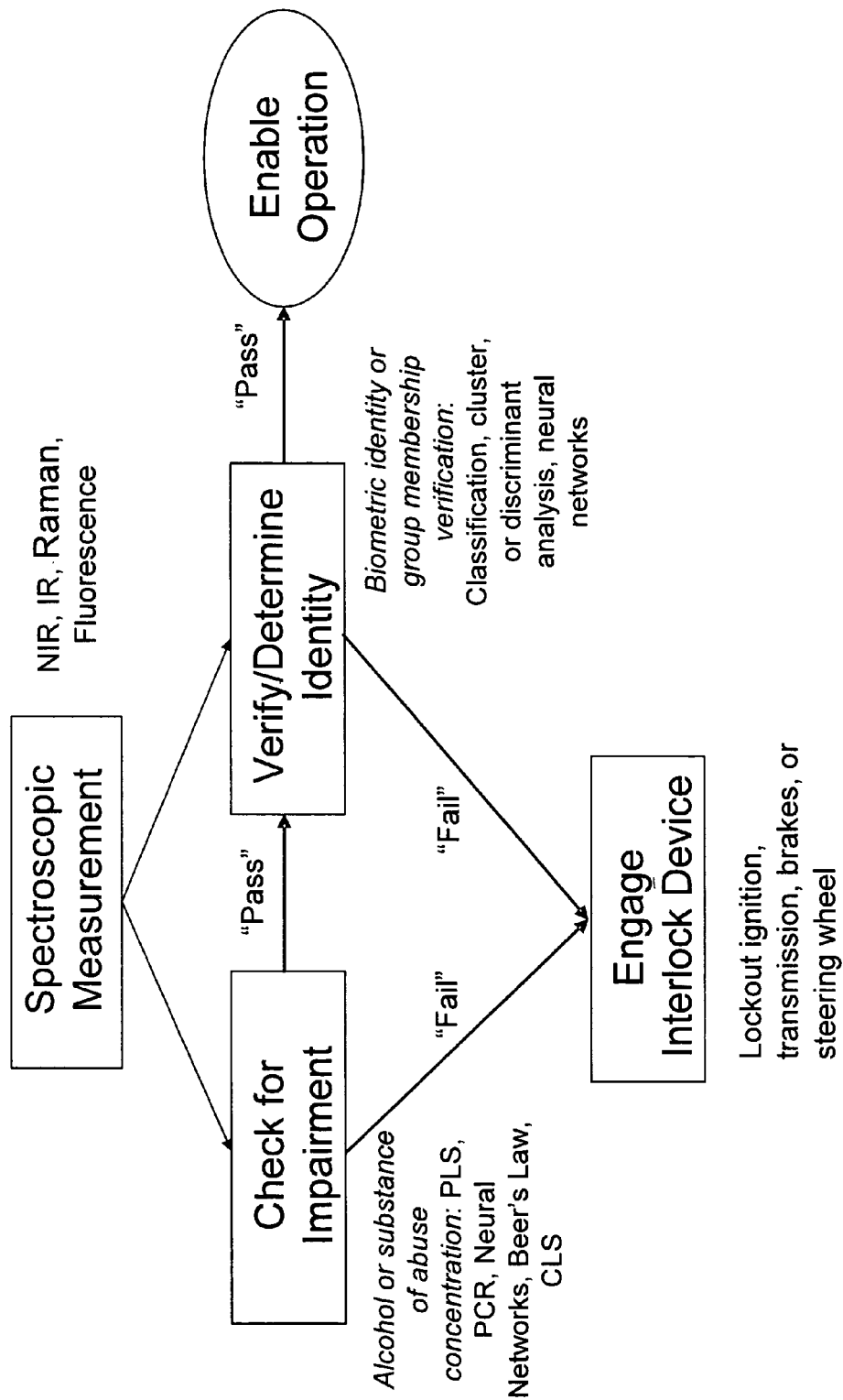
FIG. 18 is a diagram of an embodiment of an interlock embodiment known in the art.
Figure 19:
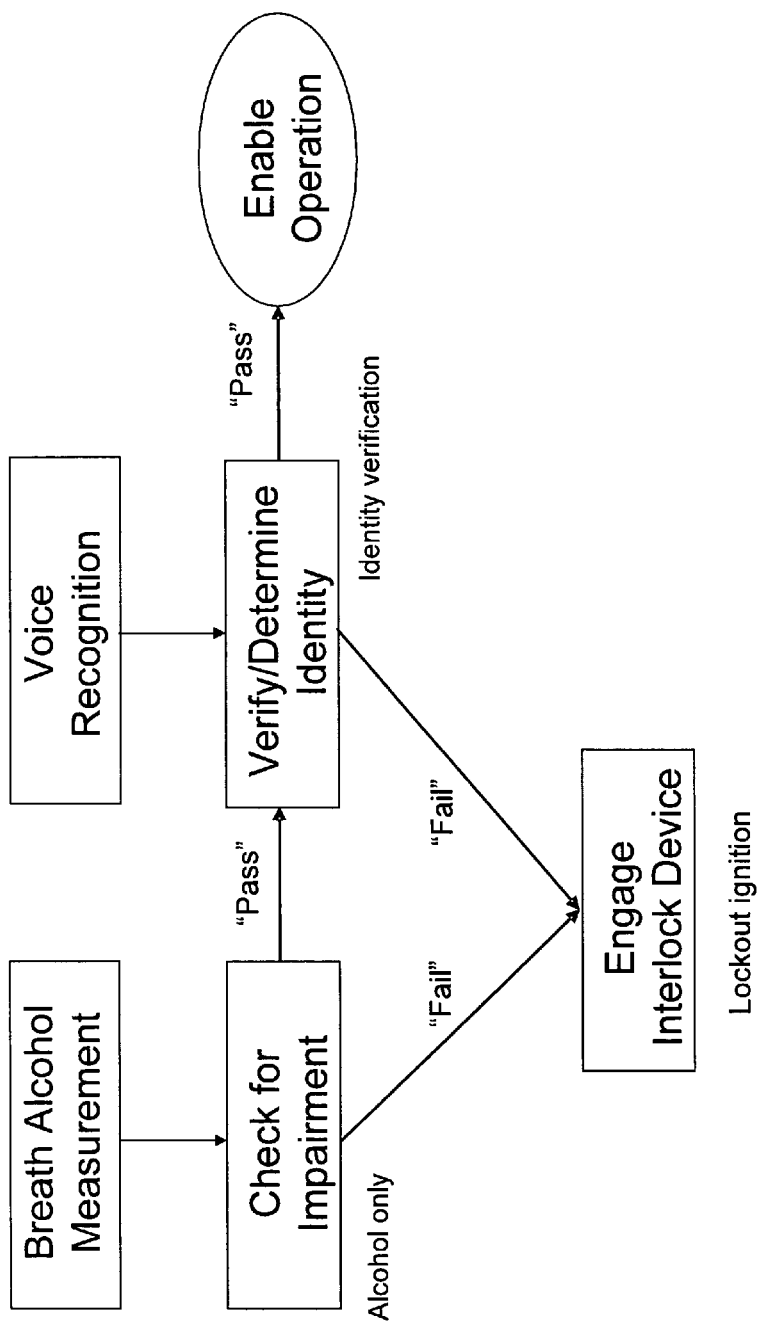
FIG. 19 is a diagram of an embodiment of a complete machinery or vehicle interlock according to the present invention.

FIGS. 18 and 19 compare a breath alcohol based interlock system for motor vehicles known in the art and an embodiment of the present invention. FIG. 18 shows the breath-based interlock which is suitable only for the detection of impairment caused by alcohol and requires a separate measurement to verify the identity of the vehicle operator. These two separate measurements are susceptible to multiple failure modes, and can allow a sober person to perform the alcohol test while an impaired person performs the identity test, allowing either a sober, unauthorized person or an impaired but otherwise authorized person to operate the vehicle. In contrast, FIG. 19 shows an embodiment of the present invention where a single spectroscopic measurement is used to determine impairment and verify identity of the operator, thus providing a significant advantage relative to existing interlock methods. Furthermore, the spectroscopic measurement of the present invention is suitable to detect impairment caused by alcohol and/or substances of abuse which significantly increases the utility of the present invention.

Remote Storage of Enrollment Data/SmartKeys

Additional security, convenience, and driver policy control can be achieved by storing user's biometric data on an external communication device rather than internally in the interlock unit. A "smartkey" which can comprise an electronic storage and communication device can be able to store, encrypt, and securely communicate data to the alcohol interlock system. Such a smartkey can enable physical access control to a vehicle by utilizing a digital two key authentication scheme. The first key can be an authorized electronic access code which is specific to a vehicle or group of vehicles that the user is authorized to drive. The second key can be linked to the user's enrollment data which can require that only the authorized driver(s) be able to use that key. This type of system can have several advantages:

First, the system can use existing technology which has been developed for secure encryption, data transmission, and authentication transactions using smart cards/tokens. Second, in applications where a driver may be required to frequently switch vehicles (fleet shipping, school bus drivers, etc.) the use of a smartkey to store biometric data allows centralized administration of both vehicle-specific and driver-specific security and alcohol policies. A driver can be enrolled in the administrator's office on a master interlock device and the resulting enrollment information and driver-specific security policy can be encoded on the driver's key. The driver is then able to perform alcohol and biometric measurements on all vehicles in the fleet, even if that driver had never before used that specific vehicle. Centralized administration tasks, e.g. restricting or revoking a driver's privileges, can be handled using a single database. Security policy updates can be relayed to the fleet's vehicles via RF uplinks or other electronic transmission means. Through the use of RF communication, a driver's smartkey can provide rapid, seamless access to the vehicle via the touch based biometric verification step. No access codes need be required by the driver Third, in applications where updated enrollment is desired, either in a fleet vehicle system, or even in a multi-vehicle family situation, a driver's enrollment measurement can become out of date on a vehicle that they seldom use. By storing the enrollment data on a driver specific smartkey, the driver can always maintain the most current enrollment information. Profile updates can be handled via two-way communication with the driver's smartkey upon successful biometric identity verification by a vehicle's alcohol interlock system. Finally, concerns regarding the theft, manipulation, or dissemination of a driver's biometric identity information can be reduced since only a single copy of that data exists, in a secure, encrypted format, under physical control of the driver.

Some embodiments for remotely storing enrollment data are comprise a means for storing data, a means for providing power, a means for communication and data transfer. The means for storing data can be any electronic or magnetic storage media consistent with the form factor desired. Some example embodiments of the means for providing power include, but are not limited to, a battery or external RF power via the communication uplink. Some example embodiments of the means for communication and data transfer include, but are not limited to, serial or other secure data protocol via RF, optical, sonic, or direct electrical connections. These components can be combined in a wide variety of possible form factors. Some examples include car key, plastic transponder, credit card style smart card, employee id badge, lapel pin, etc.

Experimental Results: Alcohol

Two clinical studies were performed in order to demonstrate the alcohol measurement capability of the present invention. The first was a calibration study based upon the hybrid calibration model approach described above. The in vitro portion of the data was a 1.0 mm pathlength spectrum of 501.65 mg/dL alcohol in water measured in transmission. The spectrum was ratioed to a 1.0 mm pathlength transmission spectrum of carbon tetrachloride and converted to absorbance. The contribution of water to the 501.65 mg/dL alcohol spectrum was removed by subtracting an absorbance spectrum of pure water scaled to the appropriate concentration to account for the displacement effects of alcohol. Given the level of dilution of the alcohol solution, this is a reasonable first approximation since water is the dominant component of the matrix and is likely not significantly affected (in a chemical sense) by the presence of the minute quantity of alcohol. The resulting water-corrected 501.65 mg/dL alcohol spectrum was normalized to unit pathlength and concentration (absorptivity per mg/dL) and pathlength scaled for tissue as shown in FIG. 16.

The in vivo calibration data consisted of noninvasive tissue spectra collected from individuals who had not consumed alcohol. The hybrid model spectra were formed by adding the alcohol pure component spectrum at various simulated alcohol "concentrations" according to the schematic process shown in FIG. 17. The concentration for each simulated spectrum was simply drawn randomly from a uniform distribution spanning the expected range of alcohol concentrations in vivo (0 to 160 mg/dL). Each spectrum was treated as completely independent of all others, so no inter- or intra-subject differences or time dependencies were incorporated in the concentration assignments. A partial least squares (PLS) calibration model was built by regressing the synthetic alcohol concentrations on the hybrid calibration spectral data. The hybrid calibration contained approximately 1500 noninvasive NIR measurements collected from 133 subjects over three months.

The second study was a prospective validation experiment where ten volunteer subjects were measured in a clinical laboratory over a period of 5 days to assess the noninvasive alcohol measurement accuracy relative to blood and breath alcohol measurements. None of these ten subjects participated in the calibration experiment, so they represented an objective and prospective assessment of the noninvasive NIR measurement performance. Subjects were consented according to an IRB-approved protocol. Alcohol doses were administered to achieve peak blood alcohol concentration (BAC) values of 120 mg/dL (0.12%) assuming ingested alcohol would be completely absorbed into the bloodstream. The subjects were asked to consume the total alcohol dose within a 20-minute time period.

Baseline capillary blood, breath, and noninvasive alcohol measurements were acquired from each subject upon arrival in order to verify zero initial blood alcohol concentration. The blood measurements were acquired using a Yellow Springs Incorporated 2700 Select blood analyzer (YSI). Breath testing was accomplished using an Intoximeters EC/IR in "quick test" mode. Each subject then consumed his or her alcohol dose. Repeated cycles of blood, breath, and noninvasive measurements were then acquired to monitor alcohol concentration throughout each subject's alcohol excursion (about 10-12 minutes per cycle). A total of 372 sets of noninvasive, blood, and breath alcohol measurements were acquired from the 10 subjects in the validation study.

Figure 20:
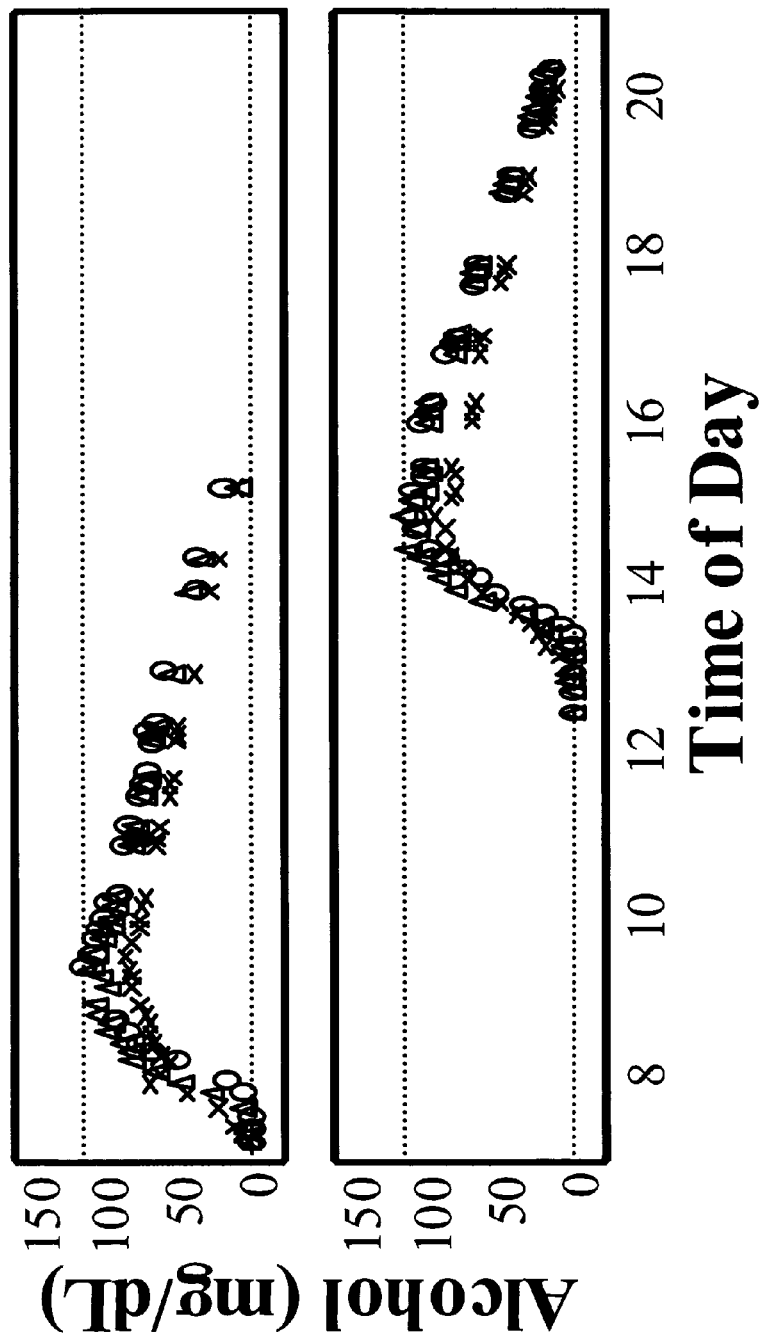
FIG. 20 shows blood, breath, and non-invasive alcohol (obtained from the present invention) over time for two subjects during induced alcohol excursions.
Figure 21:
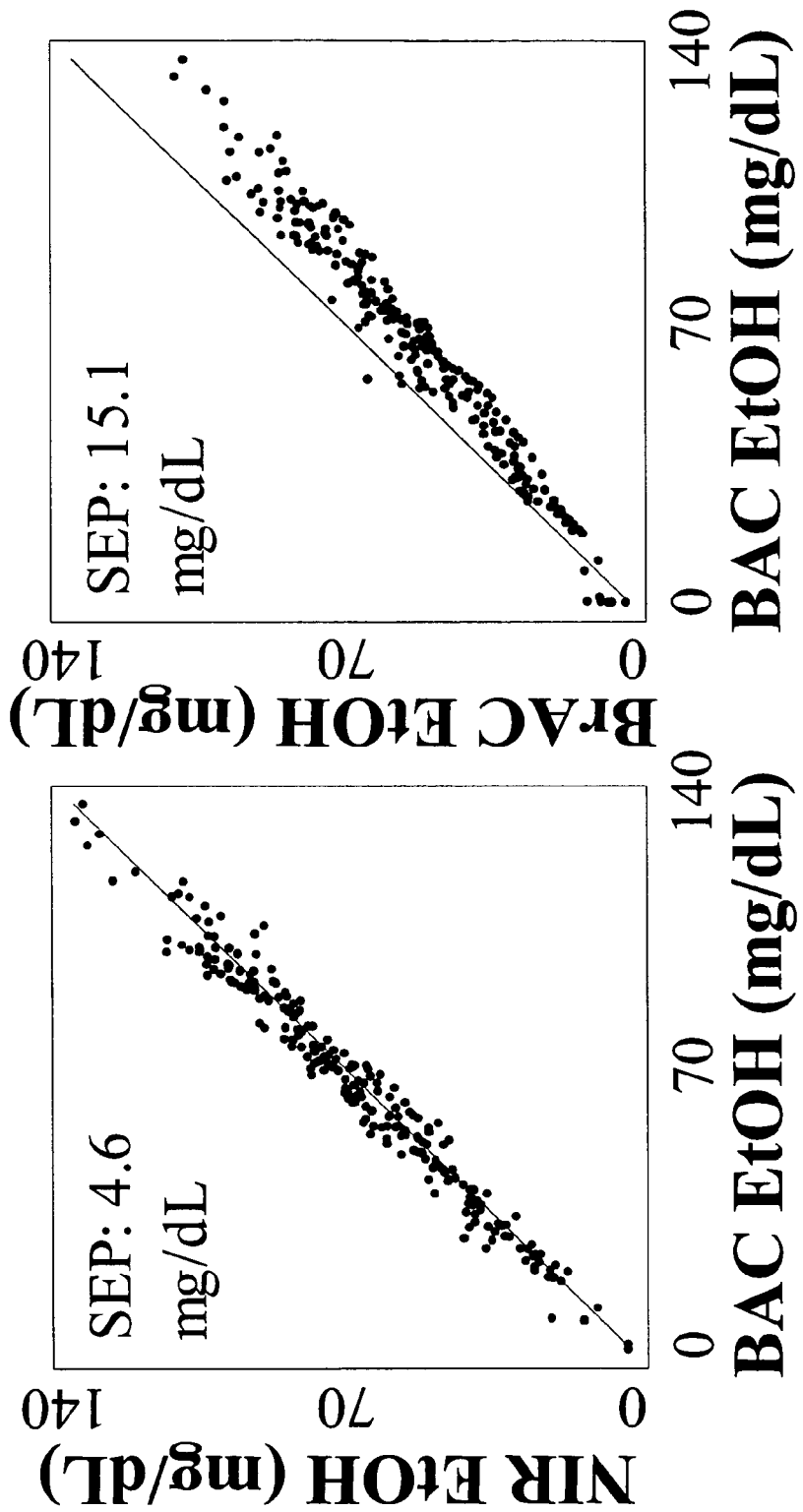
FIG. 21 is a graph of non-invasive alcohol measurements versus blood alcohol reference for multiple human subjects that demonstrates the ability of the system of the present invention to derive clinically relevant alcohol measurements.

FIG. 20 depicts the alcohol measurements acquired from two of the 10 validation subjects during their induced alcohol excursions. Each window contains the blood, breath, and noninvasive alcohol concentrations versus time that were measured during the alcohol excursion for that subject. FIG. 21 shows a side-by-side comparison of the noninvasive spectroscopic alcohol measurements of the present invention versus blood (BAC) alcohol and breath (BrAC) versus blood (BAC) alcohol that were acquired from the 10 study subjects. Examination of FIG. 19 demonstrates that the breath measurements exhibit a proportional error relative to blood alcohol. This is due to the globally applied blood-breath partition coefficient of 2100 mg EtOH/dL blood per mg EtOH/dL air that relates the concentration of alcohol in expired air from the lungs to blood alcohol. The comparison of the breath and non-invasive measurements demonstrates that under identical experimental conditions the precision of the current invention's measurement is substantially equal to that of a commonly used state-of-the-art breath alcohol instrument. In addition, the non-invasive measurement accuracy is superior to the breath measurement because it does not exhibit a proportional error.

Experimental Results: Biometric

An experiment was conducted to determine the viability of utilizing the methodology disclosed herein to verify the identification of an individual using near infrared spectroscopic measurements of skin tissue. The design of the instrumentation used was identical to that described for the experimental alcohol results discussed above. The sampling of the human tissue was done on the volar side of the forearm, consistent with the alcohol experiment. Spectra were acquired, and the recorded 4,200 to 7,200 $cm^{-1}$ NIR spectra converted to absorbance. The spectra consisted of two distinct sets. The first set was a calibration set comprised of 10,951 noninvasive spectroscopic measurements acquired from 209 subjects. On average, approximately 5 measurements were acquired from each subject for each of approximately 10 days. The second set of spectra was a validation set comprised of 3,159 noninvasive spectral measurements from 37 subjects. Each subject was measured approximately 85 times over a 2 month period.

The calibration spectra were processed to produce generic data as described in U.S. Pat. No. 6,157,041, entitled "Methods and Apparatus for Tailoring Spectroscopic Calibration Models," incorporated herein by reference. A PCA decomposition of these data was performed to generate 50 factors (also called latent variables, loadings, or eigenvectors) and associated scores (also called weights or eigenvalues). The validation measurements were then split into enrollment and test sets. The enrollment set was comprised of 37 spectra that were obtained by averaging the first three measurements acquired from each of the 37 validation subjects. The test set was comprised of the remaining validation spectra.

In order to evaluate the ability of the present invention to correctly verify the identity of a person, the enrollment spectrum of each subject was subtracted from his or her spectra in the test set. The Mahalanobis distances of the resulting "authorized" spectral differences were then calculated using the calibration factors and scores. In order to evaluate the ability to correctly reject "intruders" (a unauthorized person who claims to be authorized in order operate the machinery or vehicle), the enrollment spectrum for a given subject was subtracted from the test spectra for the other 36 validation subjects. This was done for each validation subject in round-robin fashion in order to test all possible enrollment/test permutations. Similar to the "authorized" case, the Mahalanobis distance for each of the resulting "intruder" difference spectra was computed relative to the calibration factors and scores.

The "authorized" and "intruder" Mahalanobis distances were then used to examine the biometric performance of the spectroscopic method using multiple distance thresholds. In this framework, if the distance of a given spectral difference (whether from the "authorized" or "intruder" group) is less than the threshold distance, then the purported identity is verified. The case where an "authorized" spectral difference is below the threshold (and the identity verified) is referred to as a "True Accept" (also called a True Positive or True Admission). The case where an "authorized" spectral difference is above the threshold (the device erroneously rejects an authorized user) is referred to as a "False Reject" or "False Negative". Similarly, a "True Reject" or "True Negative" occurs when an "intruder" distance is above the threshold and a "False Accept" occurs when an "intruder" distance is below the threshold.

Figure 22:
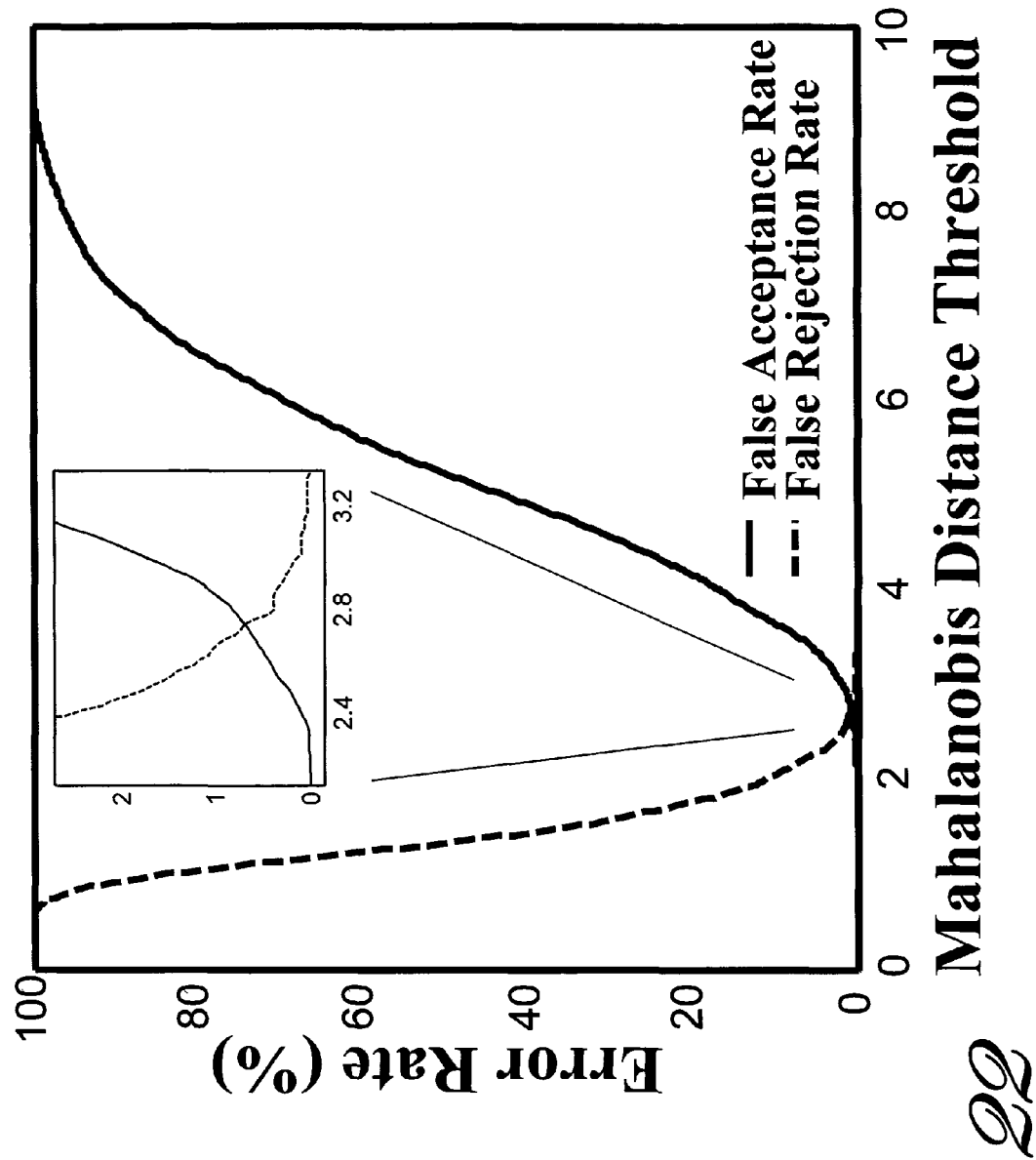
FIG. 22 shows the biometric verification false acceptance, false rejection, and equal error rates obtained using the spectroscopic method of the present invention in clinical studies.

The overall performance of a technique can be compactly summarized at a given threshold by calculating the "false acceptance rate" and the "false rejection rate". The false acceptance rate is the percentage of measurements acquired from intruders that are erroneously flagged as authorized. Conversely, the false rejection rate is the percentage of measurements acquired from authorized persons that are erroneously flagged as intruders. The threshold is a tunable variable that can be used to influence the relative security of the biometric measurement. For example, the threshold can be set to a low value (high security) that will minimize the false acceptance rate at the expense of an increase in the false rejection rate. Likewise, a low security setting would correspond to a high threshold value. In this scenario, authorized users would be rejected less frequently at the expense of an increase in intruder admission. FIG. 22 shows the false acceptance and false rejection rates at a variety of thresholds for the test data discussed above. The "equal error rate" occurs when the false acceptance and rejection rates are equal and is a common metric often used to compare biometric performance across techniques. The equal error rate for these data is approximately 0.7% demonstrating a high degree of biometric capability over an extended period of time.

The integral combination of noninvasive alcohol and biometric identity verification is also useful in applications other than vehicle and ignition interlocks. For example, similar alcohol and identity measurements are important in workplace alcohol screening, entry to secure/sensitive facilities where impairment represents a safety hazard, entry to safety sensitive work areas, entry to or presence in facilities such as prisons and jails where alcohol abstinence is required, community corrections, probation, and parole activities where alcohol abstinence is required, and alcohol treatment centers where alcohol abstinence is required.

What is claimed is:

1. A method of controlling the operation of equipment, comprising:
    a) Collecting spectral information representative of the interaction of a subject's tissue with incident radiation;
    b) Determining from the spectral information as collected in step a) an analyte property;
    c) Determining from the spectral information as collected in step a) an identity characteristic;
    d) Determining an equipment operation parameter from the analyte property and the identity characteristic;
    e) Controlling the operation of the equipment according to the equipment operation parameter.

2. A method as in claim 1, wherein collecting spectral information representative of the interaction of a subject's tissue with incident radiation comprises:
    a) directing incident radiation comprising radiation at one or more wavelengths to the tissue;
    b) collecting radiation communicated from the tissue after interaction of the tissue with the incident radiation;
    c) determining the magnitude of the collected radiation at one or more wavelengths.

3. A method as in claim 1, wherein collecting spectral information representative of the interaction of a subject's tissue with incident radiation comprises determining the response of the tissue using infrared spectroscopy, near-infrared spectroscopy, Raman spectroscopy, visible spectroscopy, fluorescence spectroscopy, or a combination thereof.

4. A method as in claim 1, wherein collecting spectral information representative of the interaction of a subject's tissue with incident radiation comprises determining the tissue's response to incident radiation using a dispersive spectrometer, interferometric/modulating spectrometer, or a combination thereof.

5. A method as in claim 1, wherein determining from the spectral information an analyte property comprises determining the presence, concentration, rate of change of concentration, direction of change of concentration, or a combination thereof, of alcohol using multivariate analysis.

6. A method as in claim 1, wherein determining from the spectral information an analyte property comprises determining the presence, concentration, rate of change of concentration, direction of change of concentration, or a combination thereof, of a substance of abuse using multivariate analysis.

7. A method as in claim 6, wherein determining from the spectral information an analyte property further comprises determining the presence, concentration, rate of change of concentration, direction of change of concentration, or a combination thereof, of alcohol using multivariate analysis.

8. A method as in claim 1, wherein determining from the spectral information an identity characteristic of the subject comprises analyzing the spectral information using a neural network, K-nearest neighbors, discriminant analysis, classification analysis, principal components analysis, or a combination thereof.

9. A method as in claim 1, wherein determining from the spectral information an identity characteristic of the subject comprises determining whether the subject is a member of a group of two or more individuals authorized to operate the equipment.

10. A method as in claim 9, wherein determining from the spectral information an identity characteristic of the subject comprises determining the specific individual in the group that matches the subject.

11. A method as in claim 1, further comprising accepting an asserted identification, and wherein determining an identity characteristic comprises determining whether the spectral information indicates that the subject identification matches the asserted identification.

12. A method as in claim 1, further comprising storing a representation of the tissue response of a first subject, and, when the identity characteristic indicates that the current subject is the first subject, then determining the analyte property from the spectral information and from the stored representation.

13. A method as in claim 12, further comprising modifying the stored representation based on the spectral information.

14. A method as in claim 1, wherein determining an equipment operation parameter and controlling the operation of the equipment according to the parameter comprises preventing an engine of the equipment from operating unless both (a) the analyte property indicates that the presence or concentration of a selected analyte has a value defined as acceptable for operation of the equipment and (b) the identity characteristic indicates that the subject is a member of a group of two or more individuals authorized to operate the equipment.

15. A method as in claim 1, wherein determining an equipment operation parameter and controlling the operation of the equipment according to the parameter comprises preventing a transmission of the equipment from engaging an engine of the equipment to move the equipment unless both (a) the analyte property indicates that the presence or concentration of a selected analyte has a value defined as acceptable for operation of the equipment and (b) the identity characteristic indicates that the subject is a member of a group of one or more individuals authorized to operate the equipment.

16. A method of claim 1, wherein the equipment is an automobile, the analyte property is the concentration of alcohol in the subject, the identity characteristic is a determination of whether the subject is a member of an authorized driver group, and operation of the equipment according to the equipment operating parameter comprises preventing the car from being driven unless (a) the alcohol concentration is below a threshold, and (b) the subject is a member of the authorized driver group.

17. A method according to claim 1, wherein controlling the operation of the equipment comprises at least one of: control operation of an ignition system associated with an engine of the equipment, control operation of a transmission system associated with the equipment, control operation of a steering system associated with the equipment, control operation of an electrical system associated with the equipment, control operation of a braking system associated with the equipment, control operation of a reporting system associated with the equipment, control operation of a recording system associated with the equipment, control operation of accessories associated with the equipment, control operation of a control computer associated with the equipment.

18. A method as in claim 1, further comprising communicating, substantially contemporaneously with determination of the equipment operation parameter, to a receiver located a distance from the equipment one or more of: (1) the analyte property; (2) the identity characteristic; (3) information determined from the analyte property, the identity characteristic, or both; or (4) a combination thereof.

19. A method as in claim 1, wherein determining an equipment operation parameter from the analyte property and the identity characteristic comprises determining an equipment operation parameter from the analyte property and the identity characteristic and a stored user access profile.

20. A method as in claim 19, wherein the stored user access profile is accessed from a device transportable by a user.

21. An apparatus for the control of the operation of equipment, comprising:
  a) A spectroscopic measurement system, adapted to determine a spectral response of a subject's tissue to incident radiation;
  b) An analysis system, adapted to determine an analyte property responsive to the spectral response and an identification characteristic responsive to the same spectral response from the spectroscopic measurement system;
  c) An equipment control system, adapted to control the operation of the equipment responsive to information from the analysis system.

22. An apparatus as in claim 21, wherein the spectral measurement system comprises:
  a) An illumination system adapted to direct incident radiation comprising radiation at one or more wavelengths to the tissue;
  b) A collection system adapted to collect radiation communicated from the tissue after interaction of the tissue with the incident radiation;
  c) A detector adapted to determine the magnitude of the collected radiation at one or more wavelengths.

23. An apparatus as in claim 21, wherein the spectroscopic measurement system comprises an infrared spectrometer, a near-infrared spectrometer, a visible spectrometer, a Raman spectrometer, a fluorescence spectrometer, or a combination thereof.

24. An apparatus as in claim 21, wherein the spectral measurement system comprises a dispersive spectrometer, interferometric/modulating spectrometer, or a combination thereof.

25. An apparatus as in claim 21, wherein the analysis system is adapted to determine the presence, concentration, rate of change of concentration, direction of change of concentration, or a combination thereof, of alcohol using multivariate analysis.

26. An apparatus as in claim 21, wherein the analysis system is adapted to determine the presence, concentration, rate of change of concentration, direction of change of concentration, or a combination thereof, of a drug of abuse using multivariate analysis.

27. An apparatus as in claim 26, wherein the analysis system is further adapted to determine the presence, concentration, rate of change of concentration, direction of change of concentration, or a combination thereof, of alcohol using multivariate analysis.

28. An apparatus as in claim 21, wherein the analysis system is adapted to analyze the spectral information using a neural network, K-nearest neighbors, discriminant analysis, classification analysis, principal components analysis, or a combination thereof, to determine an identity characteristic of the subject.

29. An apparatus as in claim 21, wherein the analysis system is adapted to determine whether the subject is a member of a group of two or more individuals authorized to operate the equipment.

30. An apparatus as in claim 29, wherein the analysis system is adapted to determine the specific individual in the group that matches the subject.

31. An apparatus as in claim 21, wherein the equipment control system is adapted to prevent an engine of the equipment from operating unless both (a) the analyte property indicates that the presence or concentration of a selected analyte has a value defined as acceptable for operation of the equipment and (b) the identity characteristic indicates that the subject is a member of a group of two or more individuals authorized to operate the equipment.

32. An apparatus as in claim 21, wherein the equipment control system is adapted to prevent a transmission of the equipment from engaging an engine of the equipment to move the equipment unless both (a) the analyte property indicates that the presence or concentration of a selected analyte has a value defined as acceptable for operation of the equipment and (b) the identity characteristic indicates that the subject is a member of a group of one or more individuals authorized to operate the equipment.

33. An apparatus as in claim 21, wherein the equipment is an automobile, the analyte property is the concentration of alcohol in the subject, the identity characteristic is a determination of whether the subject is a member of an authorized driver group, and the equipment control system comprises an interlock to preventing the car from being driven unless (a) the alcohol concentration is below a threshold, and (b) the subject is a member of the authorized driver group.

34. An apparatus as in claim 21, wherein the analysis system:
  a) stores a representation of the tissue's response for a first subject, and, when an unknown subject is presented to the system, the analysis system determines whether the unknown subject's tissue response indicates that the unknown subject is the same as the first subject, and
  b) determines an analyte property from the information from the spectral measurement system and from the stored representation.

35. An apparatus as in claim 34, wherein the analysis system modifies the stored representation using information from the spectral measurement system when the analysis system determines that the unknown subject is the same as the first subject.

36. An apparatus as in claim 21, further comprising an identity input system for receiving an asserted identity, and wherein the analysis system determines whether the information from the spectroscopic system, compared with information determined from the asserted identity, indicates that the asserted identity is the actual identity.

37. An apparatus as in claim 21, further comprising an identity input system for receiving an asserted identity, and wherein the analysis system stores a representation of the tissue response of a first subject, and, when an unknown subject is presented to the system and indicates an asserted identity, the analysis system determines whether the unknown subject's tissue response matches the stored representation, and, if so, then indicating that the unknown subject is the first subject.

38. An apparatus as in claim 37, wherein the analysis system stores a representation of the tissue response of each of a plurality of subjects.

39. An apparatus according to claim 21, wherein the equipment control system is adapted to perform at least one of: control operation of an ignition system associated with an engine of the equipment, control operation of a transmission system associated with the equipment, control operation of a steering system associated with the equipment, control operation of an electrical system associated with the equipment, control operation of a braking system associated with the equipment, control operation of a reporting system associated with the equipment, control operation of a recording system associated with the equipment, control operation of accessories associated with the equipment, control operation of a control computer associated with the equipment.

40. An apparatus as in claim 21, further comprising a communication system adapted to communicate, substantially contemporaneously with a determination from the analysis system, information from the spectroscopic measurement system, the analysis system, or both, to a receiver located a distance from the equipment.

41. An apparatus as in claim 21, further comprising a user profile reader adapted to access a user profile stored in a storage unit separable from the equipment, and wherein the equipment control system is further responsive to the user profile reader.

42. An apparatus as in claim 41, wherein the storage unit is transportable by a user.

43. An apparatus to control operation of a vehicle, comprising:
   a) An illumination system, providing radiation at one or more wavelengths;
   b) A sampling system, receiving radiation from the illumination system and communicating radiation to tissue of a subject;
   c) A spectrometer system, receiving radiation from the tissue after interaction of the tissue with radiation from the sampling system and generating a signal representative of the tissue's interaction with radiation;
   d) A data acquisition system, generating spectroscopic data responsive to the signal from the spectrometer system;
   e) An analysis system, determining an analyte property of the tissue responsive to the spectroscopic data and an identity characteristic of the subject responsive to the same spectroscopic data from the data acquisition system; and
   f) An interlock system, controlling operation of the vehicle responsive to the analyte property and the identity characteristic.

44. An apparatus as in claim 43, wherein
   a) The analysis system comprises a model relating spectroscopic information to analyte property;
   b) The analysis system comprises a representation of spectroscopic information corresponding to one or more authorized users;
   c) The analysis system determines the analyte property from the model and the spectroscopic data from the data acquisition system; and
   d) The analysis system determines the identity characteristic from the representation and the spectroscopic data from the data acquisition system.

45. An apparatus as in claim 43, further comprising a communication system adapted to communicate, substantially contemporaneously with a determination from the analysis system, information from the data acquisition system, the analysis system, or both, to a receiver located a distance from the equipment.

46. An apparatus as in claim 43, further comprising a user profile reader adapted to access a user profile stored in a storage unit separable from the equipment, and wherein the interlock system is further responsive to the user profile reader.

47. An apparatus as in claim 43, wherein the storage unit is transportable by a user.

* * * * *